US006465056B1

(12) United States Patent
Chabrecek et al.

(10) Patent No.: US 6,465,056 B1
(45) Date of Patent: Oct. 15, 2002

(54) PROCESS FOR COATING A MATERIAL SURFACE

(75) Inventors: Peter Chabrecek, Riehen; Dieter Lohmann, Münchenstein, both of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/698,544

(22) Filed: Oct. 27, 2000

(30) Foreign Application Priority Data

Oct. 27, 1999 (DE) .............................. 99810975

(51) Int. Cl.⁷ ................................. B05D 3/06
(52) U.S. Cl. ........................ 427/557; 427/301; 427/333; 427/385.5; 427/402; 427/553
(58) Field of Search ................. 427/557, 301, 427/333, 385.5, 402, 553

(56) References Cited

U.S. PATENT DOCUMENTS 5,071,732 A   12/1991   Koehler ...................... 430/272

FOREIGN PATENT DOCUMENTS

| EP | 0 632 329 A | 6/1994 |
| EP | 0 887 369 A2 | 12/1998 |
| WO | WO 96/20796 | 7/1996 |
| WO | WO 96/20919 | 7/1996 |
| WO | WO 99/15917 | 4/1999 |
| WO | WO 99/57581 A | 11/1999 |

OTHER PUBLICATIONS

European Search Report, Apr. 10, 2000.

*Primary Examiner*—Bernard Pianalto
(74) *Attorney, Agent, or Firm*—R. Scott Meece; Jian Zhou; Richard Gearhart

(57) ABSTRACT

The invention relates to a process for coating a material surface, comprising the steps of:
 (a) providing the material surface with polymer brushes comprising polymerization initiator radicals; and
 (b) graft polymerizing one or more different ethylenically unsaturated hydrophilic monomers or macromonomers onto the polymerization initiator-modified polymer brushes.

The coated articles that are obtainable by the process of the invention have desirable characteristics regarding adherence to the substrate, durability, hydrophilicity, wettability, biocompatibility and permeability and are thus useful for the manufacture of biomedical articles such as ophthalmic devices.

14 Claims, No Drawings

PROCESS FOR COATING A MATERIAL SURFACE

The present invention relates to a process for the manufacture of coated articles wherein the coating comprises a polymer having desirable characteristics regarding adherence to the substrate, durability, hydrophilicity, wettability, biocompatibility and permeability. More particular, the present invention relates to a process for the modification of the surface of an article, such as a biomedical material or article, especially a contact lens including an extended-wear contact lens wherein the articles are at least partly coated with a polymer having a "bottle-brush" type structure composed of tethered "hairy" chains.

A variety of different types of processes for preparing polymeric coatings on a substrate have been disclosed in the prior art. For example, U.S. Pat. No. 5,527,925 describes functionalized photoinitiators and also organic substrates such as contact lenses containing said photoinitiators covalently bound to their surface. In one embodiment of said disclosure, the so modified surface of the contact lens is further coated with a photopolymerizable ethylenically unsaturated monomer which is then polymerized by irradiation thus forming a novel substrate surface. With this method, however, it is not always possible to obtain the desired coating characteristics, for example wettability characteristics which are necessary for the surface of biomedical devices including contact lenses. In particular, the ability of the known materials to attract and stabilize a continuous layer of an aqueous solution, e.g. human body fluids such as tears or mucus layers, for a prolonged period of time which is an important feature for many biomedical applications is not yet satisfactory.

Surprisingly, it now has been found that articles, particularly biomedical devices such as contact lenses, with an improved wettability, water-retention ability and biocompatibility are obtained by first of all providing the article surface with a brush-type primary polymer coating comprising polymerization initiator radicals; and then grafting one or more different ethylenically unsaturated hydrophilic monomers onto the initiator-modified polymer chains that make up the brush structure.

The present invention therefore in one aspect relates to a process for coating a material surface, comprising the steps of:

(a) providing the material surface with polymer brushes comprising polymerization initiator radicals; and
(b) graft polymerizing one or more different ethylenically unsaturated hydrophilic monomers or macromonomers onto the polymerization initiator-modified polymer brushes.

Examples of materials that may be coated according to the process of the invention are quartz, ceramics, glasses, silicate minerals, silica gels, metals, metal oxides, carbon materials such as graphite or glassy carbon, natural or synthetic organic polymers, or laminates, composites or blends of said materials, in particular natural or synthetic organic polymers which are known in large number. Some examples of polymers are polyaddition and polycondensation polymers (polyurethanes, epoxy resins, polyethers, polyesters, polyamides and polyimides); vinyl polymers (polyacrylates, polymethacrylates, polystyrene, polyethylene and halogenated derivatives thereof, polyvinyl acetate and polyacrylonitrile); elastomers (silicones, polybutadiene and polyisoprene); or modified or unmodified biopolymers (collagen, cellulose, chitosan and the like).

A preferred group of materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoropolyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefines, such as fluorinated ethylene propylene, or tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another preferred group of materials to be coated are those being conventionally used for the manufacture of biomedical devices, e.g. contact lenses, which are hydrophilic per se, since reactive groups, e.g. carboxy, carbamoyl, sulfate, sulfonate, phosphate, amine, ammonium or hydroxy groups, are inherently present in the material and therefore also at the surface of a biomedical device manufactured therefrom. Such materials are known to the skilled artisan and comprise for example polyhydroxyethyl acrylate, polyhydroxyethyl methacrylate (HEMA), polyvinyl pyrrolidone (PVP), polyacrylic acid, polymethacrylic acid, polyacrylamide, polydimethylacrylamide (DMA), polyvinyl alcohol or copolymers for example from two or more monomers from the group hydroxyethyl acrylate, hydroxyethyl methacrylate, N-vinyl pyrrolidone, acrylic acid, methacrylic acid, acrylamide, dimethyl acrylamide, vinyl alcohol and the like. Typical examples are e.g. Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon or Atlafilcon.

Still another group of preferred materials to be coated are amphiphilic segmented copolymers comprising at least one hydrophobic segment and at least one hydrophilic segment which are linked through a bond or a bridge member. Examples are silicone hydrogels, for example those disclosed in PCT applications WO 96/31792 and WO 97/49740 which are herewith incorporated by reference.

The material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or a composite made therefrom.

Moreover, the material to be coated may also be an inorganic or metallic base material with or without suitable reactive groups, e.g. ceramic, quartz, or metals, such as silicon or gold, or other polymeric or non-polymeric substrates. E.g. for implantable biomedical applications, ceramics or carbohydrate containing materials such as polysaccharides are very useful. In addition, e.g. for biosensor purposes, dextran coated base materials are expected to reduce nonspecific binding effects if the structure of the coating is well controlled. Biosensors may require polysaccharides on gold, quartz, or other non-polymeric substrates.

The form of the material to be coated may vary within wide limits. Examples are particles, granules, capsules, fibres, tubes, films or membranes, preferably moldings of all kinds such as ophthalmic moldings, in particular contact lenses. The polymer brushes according to step (a) of the process of the invention may be provided, for example, by (a1) covalently binding polymerization initiator radicals to the surface;

(a2) graft polymerizing a vinyl monomer carrying a reactive group onto the initiator-modified material surface and thereby providing the surface with polymer brushes comprising reactive groups; and (a3) reacting the reactive groups of the polymer brushes with a polymerization initiator having a functional group that is coreactive with the reactive groups of the polymer brushes.

According to this embodiment of the invention, in the initial state, the material to be coated carries initiator moieties for radical polymerization covalently bound to its surface. According to a preferred embodiment of the invention, the initiator moieties are covalently bound to the surface of the material to be modified on its surface via reaction of a functional group of the material surface with a reactive group of the initiator molecule.

Suitable functional groups may be inherently (a priori) present at the surface of the material to be modified on its surface. If substrates contain too few or no reactive groups, the material surface can be modified by methods known per se, for example plasma chemical methods (see, for example, WO 94/06485), or conventional functionalization with groups such as —OH, —NH$_2$ or —CO$_2$H produced. Suitable functional groups may be selected from a wide variety of groups well known to the skilled artisan. Typical examples are e.g. hydroxy groups, amino groups, carboxy groups, carbonyl groups, aldehyde groups, sulfonic acid groups, sulfonyl chloride groups, isocyanato groups, carboxy anhydride groups, lactone groups, azlactone groups, epoxy groups and groups being replaceable by amino or hydroxy groups, such as halo groups, or mixtures thereof. Amino groups and hydroxy groups are preferred.

Polymerization initiators bound on the surface of the material to be coated are typically those that are initiating a radical polymerization of ethylenically unsaturated compounds. The radical polymerization may be induced thermally, or preferably by irradiation.

Suitable thermal polymerization initiators are known to the skilled artisan and comprise for example peroxides, hydroperoxides, azo-bis(alkyl- or cycloalkylnitriles), persulfates, percarbonates or mixtures thereof. Examples are benzoylperoxide, tert.-butyl peroxide, di-tert.-butyl-diperoxyphthalate, tert.-butyl hydroperoxide, azo-bis (isobutyronitrile), 1,1'-azo-bis (1-cyclohexanecarbonitrile), 2,2'-azo-bis(2,4-dimethylvaleronitrile), 4,4'-azo-bis(4-cyano-valeric acid, 4,4'-azo-bis(4-cyano-n-pentanol) and the like. The thermal initiators may be linked to the surface of the bulk material by methods known per se, for example as disclosed in EP-A-0378511. Initiators for the thermal polymerization are particularly functional initiators having an initiator part such as a peroxide, hydroperoxide, persulfate or azo group and in addition a functional group that is coreactive with functional groups of the substrate, particularly with —OH, —SH, —NH$_2$, epoxy, carboxyanhydride, alkylamino,—COOH or isocyanato groups. Suitable functional groups that are coreactive with the surface of the bulk material are for example a carboxy, hydroxy, epoxy or isocyanato group. A particular preferred group of thermal initiators are azo-bis($C_2$–$C_{12}$-alkane carboxylic acids) or azo-bis($C_2$–$C_{12}$-alkanols) wherein the alkane moiety in each case may be further substituted, for example, by cyano.

Initiators for the radiation-induced polymerization are particularly functional photoinitiators having a photoinitiator part and in addition a functional group that is coreactive with functional groups of the substrate, particularly with —OH, —SH, —NH$_2$, epoxy, carboxanhydride, alkylamino,—COOH or isocyanato groups. The photoinitiator part may belong to different types, for example to the thioxanthone type and preferably to the benzoin type. Suitable functional groups that are coreactive with the surface of the bulk material are for example a carboxy, hydroxy, epoxy or isocyanato group.

Preferred polymerization initiators for use in the present invention are the photoinitiators of formulae (I) and (Ia) as disclosed in U.S. Pat. No. 5,527,925, those of the formula (I) as disclosed in PCT application WO 96/20919, or those of formulae II and III including formulae IIa–IIy and IIIg as disclosed in EP-A-0281941, particularly formulae IIb, IIi, IIm, IIn, IIp, IIr, IIs, IIx and IIIg therein. The respective portion of said three documents including the definitions and preferences given for the variables in said formulae are herewith included by reference.

The polymerization initiator moieties are preferably derived from a functional photoinitiator of the formula

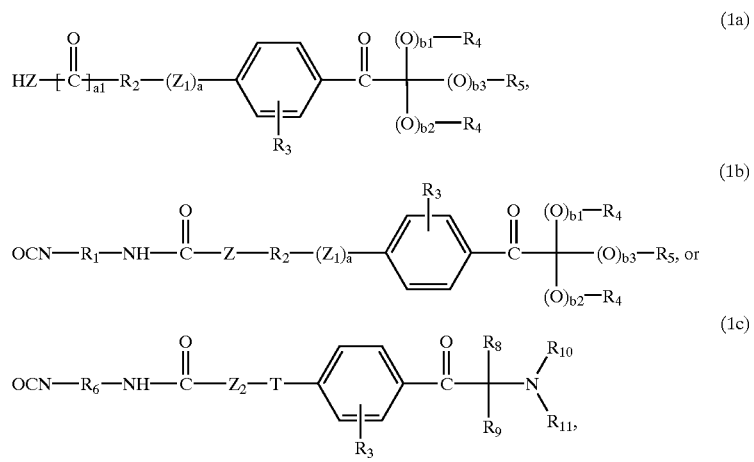

wherein Z is bivalent —O—, —NH— or —NR$_{12}$—; Z$_1$ is —O—, —O—(O)C—, —C(O)—O— or —O—C(O)—O—; R$_3$ is H, C$_1$–C$_{12}$-alkyl, C$_1$–C$_{12}$-alkoxy or N—C$_1$–C$_{12}$-alkylamino; R$_4$ and R$_5$ are each independently of the other H, linear or branched C$_1$–C$_8$-alkyl, C$_1$–C$_8$-hydroxyalkyl or C$_6$–C$_{10}$-aryl, or the groups R$_4$—(O)$_{b1}$— and R$_4$—(O)$_{b2}$— together are —(CH$_2$)$_c$— wherein c is an integer from 3 to 5, or the groups R$_4$—(O)$_{b1}$—, R$_4$—(O)$_{b2}$— and R$_5$—(O$_1$)$_{b3}$— together are a radical of the formula

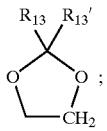

R$_2$ is a direct bond or linear or branched C$_1$–C$_8$-alkylene that is unsubstituted or substituted by —OH and/or is uninterrupted or interrupted by one or more groups —O—, —O—C(O)— or —O—C(O)—O—; R$_1$ is branched C$_3$–C$_{18}$-alkylene, unsubstituted or C$_1$–C$_4$-alkyl- or C$_1$–C$_4$-alkoxy-substituted C$_6$–C$_{10}$-arylene, or unsubstituted or C$_1$–C$_4$-alkyl- or C$_1$–C$_4$-alkoxy-substituted C$_7$–C$_{18}$-aralkylene, unsubstituted or C$_1$–C$_4$-alkyl- or C$_1$–C$_4$-alkoxy-substituted C$_3$–C$_8$-cycloalkylene, unsubstituted or C$_1$–C$_4$-alkyl- or C$_1$–C$_4$-alkoxy-substituted C$_3$–C$_8$-cyclo-alkylene-C$_y$H$_{2y}$— or unsubstituted or C$_1$–C$_4$-alkyl- or C$_1$–C$_4$-alkoxy-substituted —C$_y$H$_{2y}$-(C$_3$–C$_8$-cycloalkylene)-C$_y$H$_{2y}$— wherein y is an integer from 1 to 6; R$_6$ independently has the same definitions as R$_1$ or is linear C$_3$–C$_{18}$-alkylene; R$_{12}$ is linear or branched C$_1$–C$_6$-alkyl; T is bivalent —O—, —NH—, —S—, C$_1$–C$_8$-alkylene or

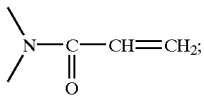

Z$_2$ is a direct bond or —O—(CH$_2$)$_d$— wherein d is an integer from 1 to 6 and the terminal CH$_2$ group of which is linked to the adjacent T in formula (10c); R$_8$ is linear or branched C$_1$–C$_8$-alkyl, C$_2$–C$_8$-alkenyl or C$_6$–C$_{10}$-aryl-C$_1$–C$_8$-alkyl; R$_9$ independently of R$_8$ has the same definitions as R$_8$ or is C$_6$–C$_{10}$-aryl, or R$_8$ and R$_9$ together are —(CH$_2$)$_e$— wherein e is an integer from 2 to 6; R$_{10}$ and R$_{11}$ are each independently of the other linear or branched C$_1$–C$_8$-alkyl that may be substituted by C$_1$–C$_4$-alkoxy, or C$_6$–C$_{10}$-aryl-C$_1$–C$_8$-alkyl or C$_2$–C$_8$-alkenyl; or R$_{10}$ and R$_{11}$ together are —(CH$_2$)$_{f1}$—Z$_3$—(CH$_2$)$_{f2}$— wherein Z$_3$ is a direct bond, —O—, —S— or —NR$_7$—, and R$_7$ is H or C$_1$–C$_8$-alkyl and f1 and f2 are each independently of the other an integer from 2 to 4; R$_{13}$ and R$_{13}$' are each independently of the other H, C$_1$–C$_8$-alkyl, C$_3$–C$_8$-cycloalkyl, benzyl or phenyl; and a, a1, b1, b2 and b3 are each independently of the other 0 or 1; subject to the provisos that b1 and b2 are each 0 when R$_{15}$ is H; that the total of (b1+b2+b3) is not exceeding 2; and that a is 0 when R$_{12}$ is a direct bond.

A preferred sub-group of compounds of formula (1a) or (1b) comprises those wherein, b1 and b2 are each 0; Z and Z$_1$ are each bivalent —O—; b3 is 0 or 1; R$_4$ is C$_1$–C$_4$-alkyl or phenyl, or both groups R$_4$ together are tetramethylene or pentamethylene; R$_5$ is C$_1$–C$_4$-alkyl or H, R$_3$ is hydrogen; a and a1 are each independently 0 or 1; R$_2$ is linear or branched C$_2$–C$_4$-alkylene, or is a direct bond, in which case a is 0; R$_1$ is branched C$_5$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-C$_y$H$_{2y}$— or —C$_y$H$_{2y}$-cyclohexyl-C$_y$H$_{2y}$— or cyclohexyl-C$_y$H$_{2y}$— or —C$_y$H$_{2y}$-cyclohexyl-C$_y$H$_{2y}$-substituted by from 1 to 3 methyl groups; and y is 1 or 2.

An especially preferred sub-group of compounds of formula (1a) or (1b) comprises those wherein, b1 and b2 are each 0, Z and Z$_1$ are each bivalent —O—, b3 is 0 or 1; R$_4$ is methyl or phenyl, or both groups R$_4$ together are pentamethylene; R$_5$ is methyl or H; R$_3$ is hydrogen; a is 1 and R$_2$ is ethylene, or a is 0 and R$_2$ is a direct bond; a1 is 0 or 1; and R$_1$ is branched C$_6$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-CH$_2$— or cyclohexyl-CH$_2$-substituted by from 1 to 3 methyl groups.

A preferred sub-group of compounds of formula (1c) comprises those wherein T is bivalent —O—, —NH—, —S— or —(CH$_2$)$_y$— wherein y is an integer from 1 to 6; Z$_2$ is a direct bond or —O—(CH$_2$)$_y$— wherein y is an integer from 1 to 6 and the terminal CH$_2$ group of which is linked to the adjacent T in formula (10c); R$_3$ is H, C$_1$–C$_{12}$-alkyl or C$_1$–C$_{12}$-alkoxy; R$_8$ is linear C$_1$–C$_8$-alkyl, C$_2$–C$_8$-alkenyl or C$_6$–C$_{10}$-aryl-C$_1$–C$_8$-alkyl; R$_9$ independently of R$_8$ has the same definitions as R$_8$ or is C$_6$–C$_{10}$-aryl, or R$_8$ and R$_9$ together are —(CH$_2$)$_e$— wherein e is an integer from 2 to 6; R$_{10}$ and R$_{11}$ are each independently of the other linear or branched C$_1$–C$_8$-alkyl that may be substituted by C$_1$–C$_4$-alkoxy, or C$_6$–C$_{10}$-aryl-C$_1$–C$_8$-alkyl or C$_2$–C$_8$-alkenyl; or R$_{10}$ and R$_{11}$ together are —(CH$_2$)$_{f1}$—Z$_3$—(CH$_2$)$_{f2}$— wherein Z$_3$ is a direct bond, —O—, —S— or —NR$_7$—, and R$_7$ is H or C$_1$–C$_8$-alkyl and f1 and f2 are each independently of the other an integer from 2 to 4; and R$_6$ is branched C$_6$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-CH$_2$— or cyclohexylene-CH$_2$-substituted by from 1 to 3 methyl groups.

An especially preferred sub-group of compounds of formula (1c) comprises those wherein T is bivalent —O—; Z$_2$ is —O—(CH$_2$)$_y$— wherein y is an integer from 1 to 4 and the terminal CH$_2$ group of which is linked to the adjacent T in formula (10c); R$_3$ is H; R$_8$ is methyl, allyl, tolylmethyl or benzyl, R$_9$ is methyl, ethyl, benzyl or phenyl, or R$_8$ and R$_9$ together are pentamethylene, R$_{10}$ and R$_{11}$ are each independently of the other C$_1$–C$_4$-alkyl or R$_{10}$ and R$_{11}$ together are —CH$_2$CH$_2$OCH$_2$CH$_2$—, and R$_6$ is branched C$_6$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-CH$_2$— or cyclohexylene-CH$_2$-substituted by from 1 to 3 methyl groups.

Some examples of especially preferred functional photoinitiators are the compounds of formulae

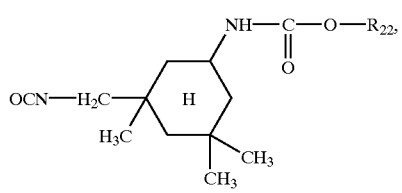

(11a)

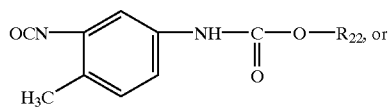

(11b)

isocyanato group of the photoinitiator, for example using a photoinitiator of the above formula (1b), (1c), (11a), (11b) or (11c). Suitable methods for this are known, for example, from the above-mentioned documents. The reaction may be carried out, for example, at elevated temperature, for example from 0° to 100° C. and preferably at room temperature, and optionally in the presence of a catalyst. After the reaction, excess compounds can be removed, for example, with solvents.

According to a preferred embodiment of the invention the material to be coated is an organic polymer containing H-active I groups, in particular —OH, —NH$_2$ and/or —NH—, on the surface that are coreactive with isocyanato groups, in some or all of them an H-atom having been substituted by a radical of formula

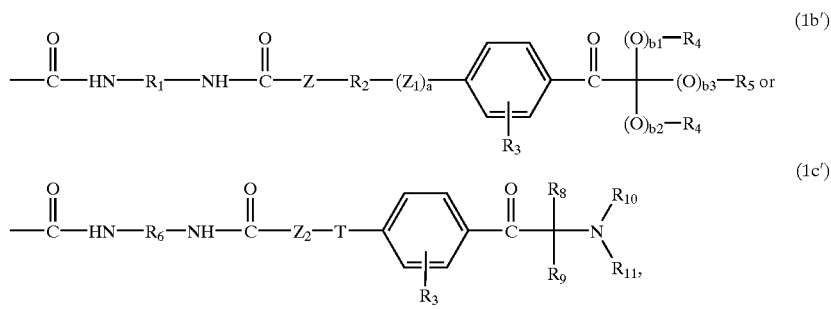

wherein R$_{22}$ is a radical

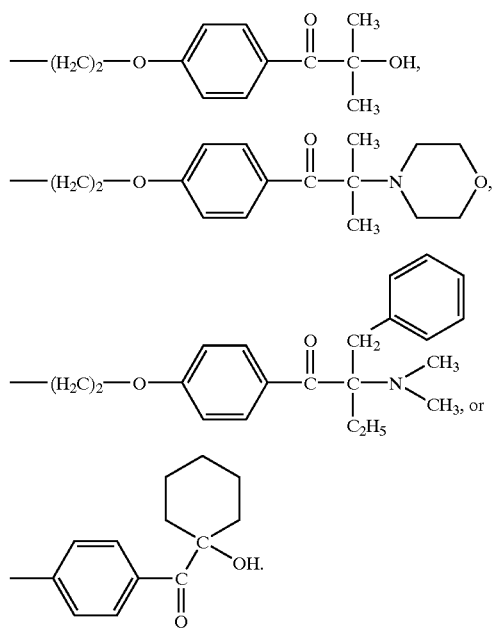

In a preferred embodiment of the invention, the covalent binding between the inorganic or preferably material surface and the photoinitiator occurs via reaction of a hydroxy, amino, alkylamino, thiol or carboxy group, particularly of a hydroxy or amino group, of the substrate surface with an wherein for the variables R$_{1-R11}$, T, Z, Z$_1$, Z$_2$, a, b1, b2 and b3 the above-given meanings and preferences apply.

According to another preferred embodiment of the invention, the covalent binding between the inorganic or preferably organic substrate and the photoinitiator occurs via reaction of a epoxy, carboxanhydride, lactone, aziactone or preferably isocyanato group of the substrate surface with a hydroxy, amino, alkylamino, thiol or carboxy group, particularly with a carboxy, hydroxy or amino group, of the photoinitiator, for example using a photoinitiator of the above formula (1a). This may be carried out, for example, by first reacting an above-mentioned bulk material containing H-active groups on the surface, in particular —OH, —NH$_2$ and/or —NH, selectively with one isocyanato group of a diisocyanate of formula OCN—R$_1$—NCO, wherein R$_1$ has the above-given meanings, and then reacting the modified bulk material with a photoinitiator of the above-mentioned formula (1a).

Suitable reactive groups of the vinyl monomer according to step (a2) are, for example, a hydroxy, amino, carboxy, carboxylic acid ester, carboxylic acid anhydride, epoxy, lactone, azlactone or isocyanato group. One group of preferred reactive groups comprises carboxy, carboxylic acid anhydride, azlactone or isocyanato, in particular isocyanato. Another group of preferred reactive groups comprises amino or in particular hydroxy.

The vinyl monomer that is grafted onto the initiator-modified surface according to step (a2) is, for example, an ethylenically unsaturated compound having from 2 to 18 C-atoms and preferably from 2 to 10 C-atoms, which is substituted by a reactive group, wherein the above-given meanings and preferences apply.

Suitable vinyl monomers having a reactive group are, for example, a compound of formula

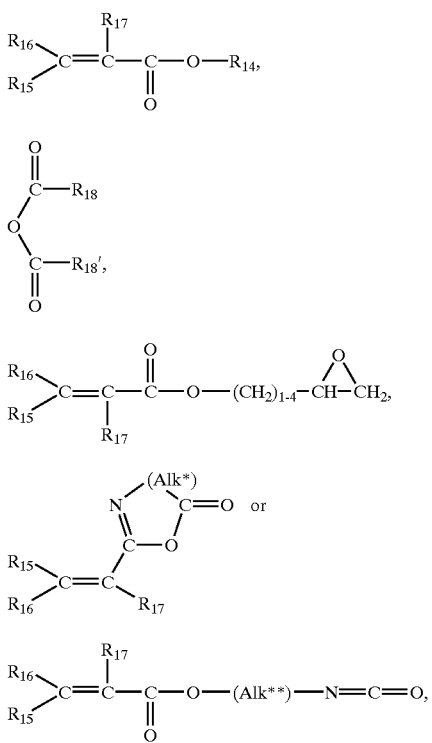

wherein $R_{14}$ is hydrogen, unsubstituted or hydroxy-substituted $C_1$–$C_6$-alkyl or phenyl, $R_{15}$, and $R_{16}$ are each independently of the other hydrogen, $C_1$–$C_4$-alkyl, phenyl, carboxy or halogen, $R_{17}$ is hydrogen, $C_1$–$C_4$-alkyl or halogen, $R_{18}$ and $R_{18}'$ are each an ethylenically unsaturated radical having from 2 to 6 C-atoms, or $R_{18}$ and $R_{18}'$ together form a bivalent radical —C($R_{15}$)=C($R_{17}$)— wherein $R_{15}$ and $R_{17}$ are as defined above, and (Alk*) is $C_1$–$C_6$-alkylene, and (Alk**) is $C_2$–$C_{12}$-alkylene.

The following preferences apply to the variables contained in formulae (2a)–(2e):

$R_{14}$ is preferably hydrogen or hydroxy-$C_1$–$C_4$-alkyl, in particular hydrogen or β-hydroxyethyl.

One of the variables $R_{15}$ and $R_{16}$ is preferably hydrogen and the other one is hydrogen, methyl or carboxy. Most preferably $R_{15}$ and $R_{16}$ are each hydrogen.

$R_{17}$ is preferably hydrogen or methyl.

$R_{18}$ and $R_{18}'$ are preferably each vinyl or 1-methylvinyl, or $R_{18}$ and $R_{18}'$ together form a radical —C($R_{15}$)=C($R_{17}$)— wherein $R_{15}$ and $R_{17}$ are each independently hydrogen or methyl.

(Alk*) is preferably methylene, ethylene or 1,1-dimethyl-methylene, in particular a radical —CH$_2$— or —C(CH$_3$)$_2$—.

(Alk**) is preferably $C_2$–$C_4$-alkylene and in particular 1,2-ethylene.

Particularly preferred vinyl monomers having a reactive group are 2-isocyanatoethylmeth-acrylate (IEM), 2-vinyl-azlactone, 2-vinyl-4,4-dimethyl-azlactone, acrylic acid, methacrylic acid, acrylic anhydride, maleic acid anhydride, 2-hydroxyethylacrylate (HEA), 2-hydroxymethacrylate (HEMA), glycidylacrylate or glycidylmethacrylat.

Throughout the application terms such as carboxy, carboxylic acid, —COOH, sulfo, —SO$_3$H, amino, —NH$_2$ and the like always include the free acid or amine as well as a suitable salt thereof, for example a biomedically or in particular occularly acceptable salt thereof such as, for example, a sodium, potassium, ammonium salt or the like (of an acid), or a hydrohalide such a hydrochloride (of an amine).

The vinyl monomer having a reactive group may be grafted as such or in admixture with a suitable vinyl comonomer, preferably a hydrophilic vinyl comonomer, onto the material surface.

The expression "hydrophilic vinyl comonomer" is understood to mean a monomer that typically produces as homopolymer a polymer that is water-soluble or capable of absorbing at least 10% by weight water.

The proportion of vinyl comonomers, if used, is preferably from 0.1 to 3 units per vinyl monomer having a reactive group, especially from 0.25 to 3 units of vinyl comonomer per vinyl monomer having a reactive group and most preferably from 0.5 to 2 units per vinyl monomer having a reactive group.

Suitable hydrophilic vinyl comonomers include, without the following being an exhaustive list, $C_1$–$C_2$-alkyl acrylates and methacrylates, acrylamide, methacrylamide, N-mono- or N,N-di-$C_1$–$C_2$-alkylacrylamide and -methacrylamide, ethoxylated acrylates and methacrylates, sodium ethylenesulfonate, sodium styrenesulfonate, 2-acrylamido-2-methylpropanesulfonic acid, N-vinylpyrrole, N-vinylsuccinimide, five- to seven-membered N-vinyl lactams, 2- or 4-vinylpyridine, amino- (the term "amino" also including quaternary ammonium), mono-$C_1$–$C_2$-alkylamino- or di-$C_1$–$C_2$-alkylamino-$C_1$–$C_2$-alkyl acrylates and methacrylates, allyl alcohol and the like. Preferred are acrylamide, N,N-di-$C_1$–$C_2$-alkyl(meth)acrylamides such as N,N-dimethyl acrylamide or five- to seven-membered N-vinyl lactams such as N-vinylpyrrolidone.

In one embodiment of the invention the vinyl monomer having a reactive group is grafted to the initiator-modified material surface in the absence of a vinyl comonomer.

The vinyl monomer having a reactive group, optionally in admixture with a vinyl comonomer, may be applied to the initiator-modified material surface and polymerized there according to processes known per se. For example, the material is immersed in a solution of the vinyl monomer(s), or a layer of vinyl monomer(s) is first of all deposited on the modified material surface, for example, by dipping, spraying, spreading, knife coating, pouring, rolling, spin coating or vacuum vapor deposition. Suitable solvents, if used in the polymerization process, are, for example, water, $C_1$–$C_4$-alcanols such as methanol or ethanol, glycols such as ethylene glycol or dipolar aprotic solvents such as, for example, acetonitrile, N,N-dimethyl formamide (DMF), N-methyl pyrrolidone (NMP), dimethyl sulfoxide (DMSO), N,N-dimethyl acetamide or acetone. The polymerization of the vinyl monomer(s) on the material surface then may be initiated, for example, thermally by the action of heat or preferably by irradiation, particularly by UV radiation. Suitable light sources for the irradiation are known to the artisan and comprise for example mercury lamps, high pressure mercury lamps, xenon lamps, carbon arc lamps or sunlight. The time period of irradiation may depend, for example, on the desired properties of the resulting composite material but is usually in the range of up to 30 minutes, preferably from 10 secondes to 10 minutes, and particularly preferably from 0.5 to 5 minutes. It is advantageous to carry out the irradiation in an atmosphere of inert gas. After the polymerization, any non-covalently bound monomers, oligomers or polymers formed can be removed, for example by treatment with suitable solvents.

In case of a thermally initiated polymerization of the vinyl monomer(s) on the material surface said polymerization may be carried out, for example, at elevated temperature, for example at a temperature of from 35 to 100° C. and preferably 40 to 80° C., for a time period of, for example, from 10 minutes to 48 hours and preferably 30 minutes to 36 hours in the absence or presence of one of the above-mentioned solvents. It is advantageous to carry out the thermally initiated polymerization in an atmosphere of inert gas.

By means of the polymerization step (a2), the vinyl monomer(s) may be grafted to the bulk material surface with formation of a primary coating comprising a plurality of polymer chains bound to the surface which form a so-called brush-type structure. Each polymer chain of said brush-type structure contains reactive groups at regular intervals (if the vinyl monomer comprising the reactive group is used without a vinyl comonomer) or statistically distributed (if the vinyl monomer comprising the reactive group is used in combination with a vinyl comonomer). The reactive groups that are present in the polymer chains are those mentioned before in the description of the vinyl monomers comprising a reactive group.

The reactive polymerization initiator of step (a3) is, for example, one of the thermal initiators or photoinitiators as mentioned in step (a1) wherein the above-given meanings and preferences apply. Preferred polymerization initiators of step (a3) are, in case of thermal initiators, azo-bis($C_2$–$C_{12}$-alkanols) which are substituted by cyano, or are, in case of photoinitiators, compounds of the above formula (1a) wherein the above given meanings and preferences apply.

The reactions of the reactive groups of the polymer brushes obtained according to step (a2) with the polymerization initiator having co-reactive groups in step (a3) are well-known in the art and may be carried out as desribed in textbooks of organic chemistry. For example, in case that the primary coating is derived from a vinyl monomer of formula (2e) or the like, the reaction of its isocyanato groups with a compound of formula (1a) may be carried out in an inert organic solvent such as acetonitrile, an optionally halogenated hydrocarbon, for example petroleum ether, methylcyclohexane, toluene, chloroform, methylene chloride and the like, or an ether, for example diethyl ether, tetrahydrofurane, dioxane, or a more polar solvent such as DMSO, DMA, N-methylpyrrolidone or even a lower alcohol or water, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. In addition, the reaction of the isocyanato groups of the polymer brushes with a compound of formula (1a) wherein HZ— is an amino group and a1 is 0, also may be carried out in an aqueous solution in the absence of a catalyst. It is advantageous to carry out the above reactions under an inert atmosphere, for example under a nitrogen or argon atmosphere.

In case that the polymer brushes are derived from a vinyl monomer of formula (2d) or the like, the reaction of the azlactone groups with a compound of formula (1a) wherein HZ— is an amino or hydroxy group and a1 is 0, may be carried out at room temperature or at elevated temperature, for example at about 20 to 75° C., in water, in a suitable organic solvent or mixtures thereof, for example in an aqueous medium or in an aprotic polar solvent such as DMF, DMSO, dioxane, acetonitrile and the like.

In case that the polymer brushes are derived from a vinyl monomer of formula (2c) or the like, the reaction of the epoxy groups with a compound of formula (1a) wherein HZ— is an amino group and a1 is 0, may be carried out, for example, at room temperature or at elevated temperature, for example at about 20 to 100° C., in water, in a suitable organic solvent or in mixtures thereof.

In case that the polymer brushes are derived from a vinyl monomer of formula (2c) or the like, the reaction of the epoxy groups with a compound of formula (1a) wherein HZ— is an hydroxy group and a1 is 0, may be carried out, for example, at room temperature or at elevated temperature, for example at about 20 to 100° C., in an aprotic medium using a base catalyst, for example Al(O—$C_1$–$C_6$-alkyl)$_3$ or Ti(O—$C_1$–$C_6$-alkyl)$_3$.

In case that the polymer brushes are derived from a vinyl monomer of formula (2b) or the like, the reaction of the carboxy anhydride with a compound of formula (1a) wherein X is an amino or hydroxy group and a1 is 0, may be carried out as described in organic textbooks, for example in an aprotic solvent, for example one of the above-mentioned aprotic solvents, at a temperature from room temperature to about 100° C.

In case that the polymer brushes are derived from a vinyl monomer of formula (2a) or the like, the reaction of its carboxy or hydroxy groups with a compound of formula (1a), wherein HZ—[C(O)$_{a1}$]— is amino, hydroxy or carboxy, may be carried out under the conditions that are customary for ester or amide formation, In case that the primary coating is derived from a vinyl monomer of formula (2a) or the like, the reaction of its carboxy groups with a compound of formula (1a), wherein HZ—[C(O)$_{a1}$]— is amino or hydroxy, or the reaction of its amino or hydroxy groups with a compound of formula (1a), wherein HZ—[C(O)$_{a1}$]— is carboxy, may be carried out under the conditions that are customary for ester or amide formation, for example in an aprotic medium at a temperature from about room temperature to about 100° C. In case of a carboxy containing compound of formula (2a) it is preferred to carry out the esterification or amidation reaction in the presence of an activating agent, for example N-ethyl-N'-(3-dimethyl aminopropyl)-carbodiimide (EDC), N-hydroxy succinimide (NHS) or N,N'-dicyclohexyl carbodiimide (DCC).

According to a further embodiment of the invention, the polymer brushes according to step (a) of the process may be provided by (a1) covalently binding polymerization initiator radicals to the surface; and (a2') graft polymerizing an ethylenically unsaturated polymerization initiator onto the initiator-modified material surface, wherein said ethylenically unsaturated polymerization initiator is a photoinitiator in case of a thermal initiator in step (a1), or is a thermal initiator in case of a photoinitiator in step (a1).

According to this embodiment of the invention, the polymerization initiator of step (a1) is preferably a thermal polymerization initiator, in particular one of the thermal polymerization initiators mentioned before; and the ethylenically unsaturated polymerization initiator of step (a2') is a photoinitiator.

A group of suitable photoinitiators according to step (a2') conforms, for example, to formula

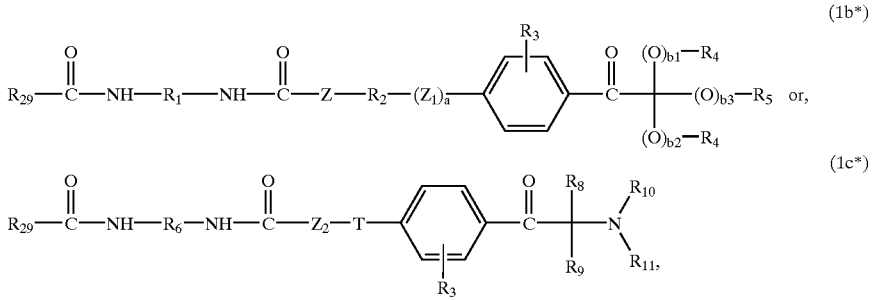

wherein for $R_1$, $R_2$, $R_3$, $R_4$, $R_5$, $R_6$, $R_8$, $R_9$, $R_{10}$, $R_{11}$, T, Z, $Z_1$, $Z_2$, b1, b2 and b3 each the above given meanings and preferences apply, and $R_{29}$ is a radical of formula

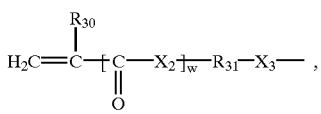 (3)

wherein $R_{30}$ is hydrogen or methyl, $R_{31}$ is $C_1$–$C_{12}$-alkylene, $C_1$–$C_6$-alkylenephenylene or phenylene-$C_1$–$C_6$-alkylene, or if w is 0 may also be a direct bond, w is 0 or 1, and $X_2$ and $X_3$ are each independently of the other —O— or —NH—. $R_{31}$ is preferably linear or branched $C_2$–$C_6$-alkylene, more preferably linear $C_2$–$C_4$-alkylene, and in particular 1,2-ethylene. w is preferably an integer of 1.

The compounds of formulae (1b*) and (1c*) are known, for example, from PCT application WO96/20919 or from U.S. Pat. No. 5,527,925.

The ethylenically unsaturated polymerization initiator may be applied to the initiator-modified material surface and polymerized there, for example, in analogy to the graft polymerization of the vinyl monomer having a reactive group as described above.

By means of the above described reaction step (a) of the process of the invention, the material surface is provided with a plurality of polymer brushes comprising polymerization initiator radicals. Each polymer chain of said brush-type structure contains polymerization initiator radicals at regular intervals (if the vinyl monomer comprising the reactive group is used without a vinyl comonomer, or if an ethylenically unsaturated polymerization initiator is used) or statistically distributed (if the vinyl monomer comprising the reactive group is used in combination with a vinyl comonomer).

A hydrophilic monomer in step (b) of the invention is understood to mean a monomer that typically produces as homopolymer a polymer that is water-soluble or capable of absorbing at least 10% by weight water.

Suitable hydrophilic vinyl comonomers include, without the following being an exhaustive list, hydroxy-substituted $C_1$–$C_4$-alkyl acrylates and methacrylates, acrylamide, methacryl-amide, mono- or di-$C_1$–$C_4$ alkylacrylamides and -methacrylamides, ethoxylated acrylates and methacrylates, hydroxy-substituted $C_1$–$C_4$-alkylacrylamides and methacrylamides, hydroxy-substituted $C_1$–$C_4$-alkyl vinyl ethers, sodium ethylenesulfonate, sodium styrenesulfonate, 2-acrylamido-2-methylpropanesulfonic acid, N-vinylpyrrole, N-vinylsuccinimide, N-vinylpyrrolidone, 2- or 4-vinylpyridine, vinylically unsaturated carboxylic acids having a total of from 3 to 5 carbon atoms, amino- (the term "amino" also including quaternary ammonium), mono-$C_1$–$C_4$-alkylamino- or di-$C_1$–$C_4$-alkylamino-$C_1$–$C_4$-alkyl acrylates and methacrylates, vinylacetate, allyl alcohol and the like. Preferred are, for example, hydroxy-substituted $C_2$–$C_4$alkyl (meth)acrylates, five- to seven-membered N-vinyl lactams, N,N-di-$C_1$–$C_4$-alkyl(meth)acrylamides, acrylic acid and methacrylic acid.

Examples of suitable hydrophilic vinyl comonomers include hydroxyethyl methacrylate, hydroxyethyl acrylate, acrylamide, methacrylamide, N,N-dimethylacrylamide, allyl alcohol, vinylpyridine, N-vinylpyrrolidine, glycerol methacrylate, N-(1,1-dimethyl-3-oxobutyl)-acrylamide and the like. Preferred hydrophilic vinyl comonomers are 2-hydroxyethyl methacylate, N-vinylpyrrolidone, N,N-dimethylacrylamide and acrylamide.

A suitable macromonomer according to step (b) of the process of the invention is, for example, of formula

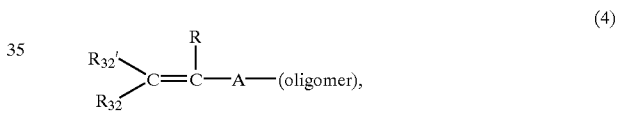 (4)

$R_{32}$ is hydrogen, $C_1$–$C_6$-alkyl or a radical —COOR';

R, R' and $R_{32}'$ are each independently of the other hydrogen or $C_1$–$C_6$-alkyl;

A is a direct bond or is a radical of formula

| —C(O)—(A$_1$)$_n$—X— | (5a) or |
| —(A$_2$)$_m$—NH—C(O)—X— | (5b); or |
| —(A$_2$)$_m$—X—C(O)— | (5c); or |
| —C(O)—NH—C(O)—X— | (5d); or |
| —C(O)—X$_1$-(alk*)-X—C(O)— | (5e); or |

A and $R_{32}$, together with the adjacent double bond, are a radical of formula

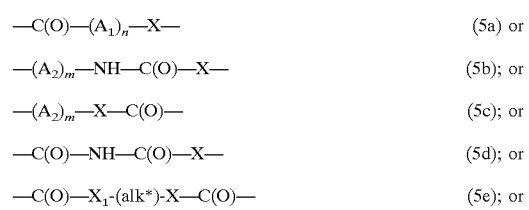 (5f)

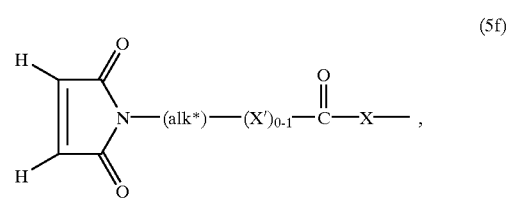

$A_1$ is —O—$C_2$–$C_{12}$-alkylene which is unsubstituted or substituted by hydroxy, or is —O—$C_2$–$C_{12}$-alkylene-NH—C(O)— or —O—$_2$–$C_{12}$-alkylene-O—C(O)—

NH—$R_{33}$—NH—C(O)— or —NH-(Alk*)-C(O)—, wherein (Alk*) is as defined above and $R_{33}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X, $X_1$ and X' are each independently of the other a bivalent group —O— or —NR", wherein R" is hydrogen or $C_1$–$C_6$-alkyl;

(alk*) is $C_2$–$C_{12}$-alkylene;

and (oligomer) denotes (i) the radical of a telomer of formula $$\text{-(alk)-S-[B]}_p\text{-[B']}_q\text{-Q} \qquad (6a),$$

wherein (alk) is $C_2$–$C_{12}$-alkylene,

Q is a monovalent group that is suitable to act as a polymerization chain-reaction terminator, p and q are each independently of another an integer from 0 to 350, wherein the total of (p+q) is an integer from 2 to 350, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula $$-[\text{CH}_2-\text{CH}_2-\text{N}]_u-\text{Q}', \qquad (6b)$$
$$\qquad\qquad\quad | $$
$$\qquad\qquad\;\; \text{O}=\text{C}$$
$$\qquad\qquad\qquad\backslash$$
$$\qquad\qquad\qquad R_{19}$$

wherein $R_{19}$ is hydrogen or unsubstituted or hydroxy-substituted $C_1$–$C_{12}$-alkyl, u is an integer from 2 to 250 and Q' is a radical of a polymerization initiator; or (iii) the radical of formula $$\text{Ph}-\text{CH}_2-[\text{N}-\text{CH}_2-\text{CH}_2]_u-\text{XH}, \qquad (6b')$$
$$\qquad\qquad\qquad\quad | $$
$$\qquad\qquad\qquad \text{C}=\text{O}$$
$$\qquad\qquad\qquad /$$
$$\qquad\qquad\qquad R_{19}$$

wherein $R_{19}$, X and u are as defined above, or (iv) the radical of an oligomer of formula $$-[\text{CH}\overset{\text{CH}_2}{\underset{|}{\diagdown}}\text{CH}-\text{CH}_2]_v-\text{Q}'', \qquad (6c)$$
$$\qquad\quad \text{N}^+ \;\; \text{An}^-$$
$$\qquad\;\; / \;\; \backslash$$
$$\qquad R_{20} \;\; R_{20}'$$

wherein $R_{20}$ and $R_{20}'$ are each independently $C_1$–$C_4$-alkyl, An is an anion, v is an integer from 2 to 250, and Q" is a monovalent group that is suitable to act as a polymerization chain-reaction terminator; or (v) the radical of an oligopeptide of formula $$-\text{CHR}_{21}-\text{C(O)}-\text{NH}]_t-\text{CHR}_{21}-\text{COOH} \qquad (6d) \text{ or}$$

$$-\text{CHR}_{21}-\text{NH}-\text{C(O)}-\text{CHR}_{21})_t-\text{NH}_2 \qquad (6d'),$$

wherein $R_{21}$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—$NH_2$ and t is an integer from 2 to 250, or the radical of an oligopeptide based on proline or hydroxyproline; or (vi) the radical of a polyalkylene oxide of formula $$(\text{alk}''-\text{O})_z-[\text{CH}_2-\text{CH}_2-\text{O}]_r[\text{CH}_2-\text{CH(CH}_3)-\text{O}]_s-R_{34} \qquad (6e),$$

wherein $R_{34}$ is hydrogen or $C_1$–$C_{24}$-alkyl, (alk") is $C_2$–$C_4$-alkylene, z is 0 or 1, r and s are each independently an integer from 0 to 250 and the total of (r+s) is from 2 to 250; or (vii) the radical of an oligosaccharide;

subject to the provisos that

A is not a direct bond if (oligomer) is a radical of formula (6a);

A is a radical of formula (5a), (5b) or (5d) or A and $R_{32}$, together with the adjacent double bond, are a radical of formula (5f) if (oligomer) is a radical of formula (6b), (6c), (6d) or (6e) or is the radical of an oligosaccharide;

A is a direct bond if (oligomer) is a radical of formula (6b'); and

A is a radical of formula (5c) or (5e) if (oligomer) is a radical of formula (6d').

The following preferences apply to the variables contained in the definition of the macromonomer of formula (4):

R' is preferably hydrogen or $C_1$–$C_4$-alkyl, more preferably hydrogen or $C_1$–$C_2$-alkyl and particularly preferably hydrogen.

$R_{32}$ is preferably hydrogen, methyl or carboxyl, and particularly preferably hydrogen.

R is preferably hydrogen or methyl.

X is preferably a bivalent group —O— or —NH—. X is particularly preferably the group —NH— if (oligomer) is a radical of formula (6a); (6c) or (6d), and is particularly preferably the group —O— if (oligomer) is a radical of formula (6b) or (6e) or is the radical of an oligosaccharide. X' is preferably —O— or —NH— and more preferably —NH—. $X_1$ is preferably —O— or —NH—.

$R_{33}$ as alkylene is preferably a linear or branched $C_3$–$C_{14}$alkylene radical, more preferably a linear or branched $C_4$–$C_{12}$alkylene radical and most preferably a linear or branched $C_6$–$C_{10}$-alkylene radical. Some preferred alkylene radicals are 1,4-butylene, 2,2-dimethyl-1,4-butylene, 1,5-pentylene, 2,2-dimethyl-1,5-pentylene, 1,6-hexylene, 2,2,3- or 2,2,4-trimethyl-1,5-pentylene, 2,2-dimethyl-1,6-hexylene, 2,2,3- or 2,2,4- or 2,2,5-trimethyl-1,6-hexylene, 2,2-dimethyl-1,7-heptylene, 2,2,3- or 2,2,4- or 2,2,5- or 2,2,6-trimethyl-1,7-heptylene, 1,8-octylene, 2,2-dimethyl-1,8-octylene and 2,2,3- or 2,2,4- or 2,2,5- or 2,2,6- or 2,2,7-trimethyl-1,8-octylene.

When $R_{33}$ is arylene, it is, for example, naphthylene or especially phenylene, each of which may be substituted, for example, by $C_1$–$C_4$-alkyl or by $C_1$–$C_4$-alkoxy. Preferably, $R_{33}$ as arylene is 1,3- or 1,4-phenylene that is unsubstituted or substituted by $C_1$–$C_4$-alkyl or by $C_1$–$C_4$-alkoxy in the ortho-position to at least one linkage site.

$R_{33}$ as aralkylene is preferably naphthylalkylene and most preferably phenylalkylene. The alkylene group in aralkylene contains preferably from 1 to 12, more preferably from 1 to 6 and most preferably from 1 to 4 carbon atoms. Most preferably, the alkylene group in aralkylene is methylene or ethylene.

When $R_{33}$ is cycloalkylene, it is preferably $C_5$–$C_6$-cycloalkylene and most preferably cyclohexylene that is unsubstituted or substituted by methyl.

When $R_{33}$ is cycloalkylene-alkylene, it is preferably cyclopentylene-$C_1$–$C_4$-alkylene and especially cyclohexylene-$C_1$–$C_4$-alkylene, each unsubstituted or mono- or poly-substituted by $C_1$–$C_4$-alkyl, especially methyl. More preferably, the group cycloalkylene-alkylene is cyclohexylene-ethylene and, most preferably, cyclohexylene-methylene, each unsubstituted or substituted in the cyclohexylene radical by from 1 to 3 methyl groups.

When $R_{33}$ is alkylene-cycloalkylene-alkylene, it is preferably $C_1$–$C_4$-alkylene-cyclopentylene-$C_1$–$C_4$-alkylene and especially $C_1$–$C_4$-alkylene-cyclohexylene-$C_1$–$C_4$-alkylene, each unsubstituted or mono- or poly-substituted by $C_1$–$C_4$-alkyl, especially methyl. More preferably, the group alkylene-cycloalkylene-alkylene is ethylene-cyclohexylene-ethylene and, most preferably, is methylene-cyclohexylene-methylene, each unsubstituted or substituted in the cyclohexylene radical by from 1 to 3 methyl groups.

$R_{33}$ as $C_3$–$C_8$-cycloalkylene-$C_1$–$C_2$-alkylene-$C_3$–$C_8$-cycloalkylene or $C_6$–$C_{10}$-arylene-$C_1$–$C_2$-alkylene-$C_6$–$C_{10}$-arylene is preferably $C_5$–$C_6$-cycloalkylene-methylene-$C_5$–$C_6$-cycloalkylene or phenylene-methylene-phenylene, each of which may be unsubstituted or substituted in the cycloalkyl or phenyl ring by one or more methyl groups.

The radical $R_{33}$ has a symmetrical or, preferably, an asymmetrical structure. A preferred group of radicals $R_{11}$ comprises those, wherein $R_{33}$ is linear or branched $C_6$–$C_{10}$alkylene; cyclohexylene-methylene or cyclohexylene-methylene-cyclohexylene each unsubstituted or substituted in the cyclohexyl moiety by from 1 to 3 methyl groups; or phenylene or phenylene-methylene-phenylene each unsubstituted or substituted in the phenyl moiety by methyl. The bivalent radical $R_{33}$ is derived preferably from a diisocyanate and most preferably from a diisocyanate selected from the group isophorone diisocyanate (IPDI), toluylene-2,4-diisocyanate (TDI), 4,4'-methylenebis(cyclohexyl isocyanate), 1,6-diisocyanato-2,2,4-trimethyl-n-hexane (TMDI), methylenebis(phenyl isocyanate), methylenebis(cyclohexyl-4-isocyanate) and hexamethylene diisocyanate (HMDI).

Preferred meanings of $A_1$ are unsubstituted or hydroxy-substituted —O—$C_2$–$C_8$-alkylene or a radical —O—$C_2$–$C_6$-alkylene—NH—C(O)— and particularly —O—$(CH_2)_{2-4}$—, —O—$CH_2$—CH(OH)—$CH_2$— or a radical —O—$(CH_2)_{2-4}$—NH—C(O)—. A particularly preferred meaning of $A_1$ is the radical —O—$(CH_2)_2$—NH—C(O)—.

$A_2$ is preferably $C_1$–$C_6$-alkylene, phenylene or benzylene, more preferably $C_1$–$C_4$-alkylene and even more preferably $C_1$–$C_2$-alkylene.

n is an integer of 0 or preferably 1. m is preferably an integer of 1.

$R_{32}'$ is preferably hydrogen or methyl and particularly preferably hydrogen.

In case that (oligomer) is a radical of formula (6a), (6b), (6c), (6d) or (6e) or is the radical of an oligosaccharide, is A preferably a radical of formula (5a) or (5b) and particularly preferably a radical of formula (5a), wherein the above given meanings and preferences apply for the variables contained therein.

A preferred group of hydrophilic macromonomers according to the invention comprises compounds of the above formula (4), wherein R is hydrogen or methyl, $R_{32}$ is hydrogen, methyl or carboxyl, $R_{32}'$ is hydrogen, A is a radical of the formula (5a) or (5b) and (oligomer) is a radical of formula (6a), (6b), (6c), (6d) or (6e) or is the radical of an oligosaccharide. An even more preferred group of hydrophilic macromonomers comprises compounds of the above formula (4), wherein R is hydrogen or methyl, $R_{32}$ and $R_{32}'$ are each hydrogen, A is a radical of the formula (5a) and (oligomer) is a radical of formula (6a). A further group of preferred macromonomers comprises compounds of formula (4), wherein A is a radical of formula (5e) above and (oligomer) is a radical of formula (6a).

(alk) and (alk*) are each independently preferably $C_2$–$C_8$-alkylene, more preferably $C_2$–$C_6$-alkylene, even more preferably $C_2$–$C_4$-alkylene and particularly preferably 1,2-ethylene. The alkylene radicals (alk) and (alk*) may be branched or preferably linear alkylene radicals.

Q is for example hydrogen.

The total of (p+q) is preferably an integer from 2 to 150, more preferably from 5 to 100, even more preferably from 5 to 75 and particularly preferably from 10 to 50. In a preferred embodiment of the invention q is 0 and p is an integer from 2 to 250, preferably from 2 to 150, more preferably from 5 to 100, even more preferably from 5 to 75 and particularly preferably from 10 to 50.

Suitable hydrophilic substituents of the radicals B or B' may be non-ionic, anionic, cationic or zwitterionic substituents. Accordingly, the telomer chain of formula (5a) that contains monomer units B and/or B' may be a charged chain containing anionic, cationic and/or zwitterionic groups or may be an uncharged chain. In addition, the telomer chain may comprise a copolymeric mixture of uncharged and charged units. The distribution of the charges within the telomer, if present, may be random or blockwise.

In one preferred embodiment of the invention, the telomer radical of formula (6a) is composed solely of non-ionic monomer units B and/or B'. In another preferred embodiment of the invention, the telomer radical of formula (6a) is composed solely of ionic monomer units B and/or B', for example solely of cationic monomer units or solely of anionic monomer units. Still another preferred embodiment of the invention is directed to telomer radicals of formula (6a) comprising nonionic units B and ionic units B'.

Suitable non-ionic substituents of B or B' include for example a radical $C_1$–$C_6$-alkyl which is substituted by one or more same or different substituents selected from the group consisting of —OH, $C_1$–$C_4$-alkoxy and —$NR_{23}R_{23}'$, wherein $R_{23}$ and $R_{23}'$ are each independently of another hydrogen or unsubstituted or hydroxy-substituted $C_1$–$C_6$-alkyl or phenyl; phenyl which is substituted by hydroxy, $C_1$–$C_4$-alkoxy or —$NR_{23}R_{23}'$, wherein $R_{23}$ and $R_{23}'$ are as defined above; a radical —COOY, wherein Y is $C_1$–$C_{24}$-alkyl which is unsubstituted or substituted, for example, by hydroxy, $C_1$–$C_4$-alkoxy, —O—Si$(CH_3)_3$, —$NR_{23}R_{23}'$ wherein $R_{23}$ and $R_{23}'$ are as defined above, a radical —O—$(CH_2CH_2O)_{1-24}$-E wherein E is hydrogen or $C_1$–$C_6$-alkyl, or a radical —NH—C(O)—O—G, wherein —O—G is the radical of a saccharide with 1 to 8 sugar units or is a radical —O—$(CH_2CH_2O)_{1-24}$-E, wherein E is as defined above, or Y is $C_5$–$C_8$-cycloalkyl which is unsubstituted or substituted by $C_1$–$C_4$-alkyl or $C_1$–$C_4$-alkoxy, or is unsubstituted or $C_1$–$C_4$-alkyl- or $C_1$–$C_4$-alkoxy-substituted phenyl or $C_7$–$C_{12}$-aralkyl; —CONY$_1$Y$_2$ wherein Y$_1$ and Y$_2$ are each independently hydrogen, $C_1$–$C_{12}$-alkyl, which is unsubstituted or substituted for example by hydroxy, $C_1$–$C_4$-alkoxy or a radical —O—(CH$_2$CH$_2$O)$_{1-24}$-E wherein E is as defined above, or Y$_1$ and Y$_2$ together with the adjacent N-atom form a five- or six-membered heterocyclic ring having no additional heteroatom or one additional oxygen or nitrogen atom; a radical —OY$_3$, wherein Y$_3$ is hydrogen; or $C_1$–$C_{12}$-alkyl which is unsubstituted or substituted by —NR$_{23}$R$_{23}$'; or is a radical —C(O)—$C_1$–$C_4$-alkyl; and wherein R$_{23}$ and R$_{23}$' are as defined above; or a five- to seven-membered heterocyclic radical having at least one N-atom and being bound in each case via said nitrogen atom.

Suitable anionic substituents of B or B' include for example $C_1$–$C_6$-alkyl which is substituted by —SO$_3$H, —OSO$_3$H, —OPO$_3$H$_2$ and —COOH; phenyl which is substituted by one or more same or different substituents selected from the group consisting of —SO$_3$H, —COOH, —OH and —CH$_2$—SO$_3$H; —COOH; a radical —COOY$_4$, wherein Y$_4$ is $C_1$–$C_{24}$-alkyl which is substituted for example by —COOH, —SO$_3$H, —OSO$_3$H, —OPO$_3$H$_2$ or by a radical —NH—C(O)—O—G' wherein G' is the radical of an anionic carbohydrate; a radical —CONY$_5$Y$_6$ wherein Y$_5$ is $C_1$–$C_{24}$-alkyl which is substituted by —COOH, —SO$_3$H, —OSO$_3$H, or —OPO$_3$H$_2$ and Y$_6$ independently has the meaning of Y$_5$ or is hydrogen or $C_1$–$C_{12}$-alkyl; or —SO$_3$H; or a salt thereof, for example a sodium, potassium, ammonium or the like salt thereof.

Suitable cationic substituents of B or B' include $C_1$–$C_{12}$-alkyl which is substituted by a radical —NR$_{23}$R$_{23}$'R$_{23}$"$^+$An$^-$, wherein R$_{23}$, R$_{23}$' and R$_{23}$" are each independently of another hydrogen or unsubstituted or hydroxy-substituted $C_1$–$C_6$-alkyl or phenyl, and An$^-$ is an anion; or a radical —C(O)OY$_7$, wherein Y$_7$ is $C_1$–$C_{24}$-alkyl which is substituted by —NR$_{23}$R$_{23}$'R$_{23}$"$^+$An$^-$ and is further unsubstituted or substituted for example by hydroxy, wherein R$_{23}$ R$_{23}$', R$_{23}$" and An$^-$ are as defined above.

Suitable zwitterionic substituents of B or B' include a radical —R$_{24}$—Zw, wherein R$_{24}$ is a direct bond or a functional group, for example a carbonyl, carbonate, amide, ester, dicarboanhydride, dicarboimide, urea or urethane group; and Zw is an aliphatic moiety comprising one anionic and one cationic group each.

The following preferences apply to the hydrophilic substituents of B and B':

(i) Non-ionic Substituents:

Preferred alkyl substituents of B or B' are $C_1$–$C_4$-alkyl, in particular $C_1$–$C_2$-alkyl, which is substituted by one or more substituents selected from the group consisting of —OH and —NR$_{23}$R$_{23}$', wherein R$_{23}$ and R$_{23}$' are each independently of another hydrogen or $C_1$–$C_4$-alkyl, preferably hydrogen, methyl or ethyl and particularly preferably hydrogen or methyl, for example —CH$_2$—NH$_2$, —CH$_2$—N(CH$_3$)$_2$.

Preferred phenyl substituents of B or B' are phenyl which is substituted by —NH$_2$ or N(C$_1$–C$_2$-alkyl)$_2$, for example o-, m- or p-aminophenyl.

In case that the hydrophilic substituent of B or B' is a radical —COOY, Y as optionally substituted alkyl is preferably $C_1$–$C_{12}$-alkyl, more preferably $C_1$–$C_6$-alkyl, even more preferably $C_1$–$C_4$-alkyl and particularly preferably $C_1$–$C_2$-alkyl, each of which being unsubstituted or substituted as mentioned above. In case that the alkyl radical Y is substituted by —NR$_{23}$R$_{23}$', the above-given meanings and preferences apply for R$_{23}$ and R$_{23}$'. Examples of suitable saccharide substituents —O—G of the alkyl radical Y that is substituted by —NH—C(O)—O—G are the radical of a mono- or disaccharide, for example glucose, acetyl glucose, methyl glucose, glucosamine, N-acetyl glucosamine, glucono lactone, mannose, galactose, galactosamine, N-acetyl galactosamine, fructose, maltose, lactose, fucose, saccharose or trehalose, the radical of an anhydrosaccharide such as levoglucosan, the radical of a glucosid such as octylglucosid, the radical of a sugar alcohol such as sorbitol, the radical of a sugar acid derivative such as lactobionic acid amide, or the radical of an oligosaccharide with a maximum of 8 sugar units, for example fragments of a cyclodextrin, starch, chitosan, maltotriose or maltohexaose. The radical —O—G preferably denotes the radical of a mono- or disaccharide or the radical of a cyclodextrin fragment with a maximum of 8 sugar units. Particular preferred saccharide radicals —O—G are the radical of trehalose or the radical of a cyclodextrin fragment. In case that the alkyl radical Y is substituted by a radical —O—(CH$_2$CH$_2$O)$_{1-24}$-E or —NH—C(O)—O—G wherein —O—G is —O—(CH$_2$CH$_2$O)$_{1-24}$-E, the number of (CH$_2$CH$_2$O) units is preferably from 1 to 12 in each case and more preferably from 2 to 8. E is preferably hydrogen or $C_1$–$C_2$-alkyl.

Y as $C_5$–$C_8$-cycloalkyl is for example cyclopentyl or preferably cyclohexyl, each of which being unsubstituted or substituted for example by 1 to 3 $C_1$–$C_2$-alkyl groups. Y as $C_7$–$C_{12}$-aralkyl is for example benzyl.

Preferred nonionic radicals —COOY are those wherein Y is $C_1$–$C_6$-alkyl; or $C_2$–$C_6$-alkyl which is substituted by one or two substituents selected from the group consisting of hydroxy; $C_1$–$C_2$-alkoxy; —O—Si(CH$_3$)$_3$; and —NR$_{23}$R$_{23}$' wherein R$_{23}$ and R$_{23}$' are each independently of another hydrogen or $C_1$–$C_4$-alkyl; or Y is a radical —CH$_2$CH$_2$—O—(CH$_2$CH$_2$O)$_{1-12}$-E wherein E is hydrogen or $C_1$–$C_2$-alkyl; or is a radical —C$_2$–C$_4$-alkylene—NH—C(O)—O—G, wherein —O—G is the radical of a saccharide.

More preferred non-ionic radicals —COOY are those wherein Y is $C_1$–$C_4$-alkyl; or $C_2$–$C_4$-alkyl which is substituted by one or two substituents selected from the group consisting of —OH and —NR$_{23}$R$_{23}$' wherein R$_{23}$ and R$_{23}$' are each independently of another hydrogen or $C_1$–$C_2$-alkyl; or a radical —CH$_2$CH$_2$—O—(CH$_2$CH$_2$O)$_{1-12}$-E wherein E is hydrogen or $C_1$–$C_2$-alkyl; or is a radical —C$_2$–C$_4$-alkylene—NH—C(O)—O—G wherein —O—G is the radical of a saccharide.

Particularly preferred radicals —COOY comprise those wherein Y is $C_1$–$C_2$-alkyl, particularly methyl; or $C_2$–$C_3$-alkyl, which is unsubstituted or substituted by hydroxy or N,N-di-$C_1$–$C_2$-alkylamino, or is a radical -$C_2$–$C_3$-alkylene—NH—C(O)—O—G wherein —O—G is the radical of trehalose or the radical of a cyclodextrin fragment with a maximum of 8 sugar units.

Preferred non-ionic substituents —C(O)—NY$_1$Y$_2$ of B or B' are those wherein Y$_1$ and Y$_2$ are each independently of the other hydrogen or $C_1$–$C_6$-alkyl which is unsubstituted or substituted by hydroxy; or Y$_1$ and Y$_2$ together with the adjacent N-atom form a heterocyclic 6-membered ring having no further heteroatom or having one further N- or O-atom. Even more preferred meanings of Y$_1$ and Y$_2$, independently of each other, are hydrogen or $C_1$–$C_4$-alkyl which is unsubstituted or substituted by hydroxy; or Y$_1$ and Y$_2$ together with the adjacent N-atom form a N—$C_1$–$C_2$-alkylpiperazino or morpholino ring. Particularly preferred non-ionic radicals —C(O)—NY$_1$Y$_2$ are those wherein Y$_1$ and Y$_2$ are each independently of the other hydrogen or $C_1$–$C_2$-alkyl; or Y$_1$ and Y$_2$ together with the adjacent N-atom form a morpholino ring.

Preferred non-ionic substituents —OY$_3$ of B or B' are those wherein Y$_3$ is hydrogen, $C_1$–$C_4$-alkyl which is unsubstituted or substituted by —NH$_2$ or —N(C$_1$–C$_2$-alkyl)$_2$, or is a group —C(O)C$_1$–C$_2$-alkyl. Y$_3$ is particularly preferred hydrogen or acetyl.

Preferred non-ionic heterocyclic substituents of B or B' are a 5- or 6-membered heteroaromatic or heteroaliphatic radical having one N-atom and in addition no further heteroatom or an additional N- or O-heteroatom, or is a 5 to 7-membered lactame. Examples of such heterocyclic radicals are N-pyrrolidonyl, 2- or 4-pyridinyl, 2-methyl pyridin-5-yl, 2-, 3- oder 4-hydroxypyridinyl, N-ε-caprolactamyl, N-imidazolyl, 2-methylimidazol-1-yl, N-morpholinyl or 4-N-methylpiperazin-1-yl, particularly N-morpholinyl or N-pyrrolidonyl.

A group of preferred non-ionic substituents of B or B' comprises C$_1$–C$_2$-alkyl, which is unsubstituted or substituted by —OH or —NR$_{23}$R$_{23}$', wherein R$_{23}$ and R$_{23}$' are each independently of the other hydrogen or C$_1$–C$_2$-alkyl; a radical —COOY wherein Y is C$_1$–C$_4$-alkyl; C$_2$–C$_4$-alkyl which is substituted by —OH, —NR$_{23}$R$_{23}$' wherein R$_{23}$ and R$_{23}$' are each independently of another hydrogen or C$_1$–C$_2$-alkyl, or Y is a radical —C$_2$–C$_4$-alkylene—NH—C(O)—O—G wherein —O—G is the radical of a saccharide; a radical —C(O)—NY$_1$Y$_2$, wherein Y$_1$ and Y$_2$ are each independently of the other hydrogen or C$_1$–C$_6$-alkyl which is unsubstituted or substituted by hydroxy, or Y$_1$ and Y$_2$ together with the adjacent N-atom form a heterocyclic 6-membered ring having no further heteroatom or having one further N- or O-atom; a radical —OY$_3$, wherein Y$_3$ is hydrogen, C$_1$–C$_4$-alkyl which is unsubstituted or substituted by —NH$_2$ or —N(C$_1$–C$_2$-alkyl)$_2$, or is a group —C(O)C$_1$–C$_2$-alkyl; or a 5- or 6-membered heteroaromatic or heteroaliphatic radical having one N-atom and in addition no further heteroatom or an additional N-, O- or S-heteroatom, or a 5 to 7-membered lactame.

A group of more preferred non-ionic substituents of B or B' comprises a radical —COOY, wherein Y is C$_1$–C$_2$-alkyl, C$_2$–C$_3$-alkyl, which is substituted by hydroxy, amino or N,N-di-C$_1$–C$_2$-alkylamino, or is a radical —C$_2$–C$_4$-alkylene—NH—C(O)—O—G wherein —O—G is the radical of trehalose or a cyclodextrin fragment with a maximum of 8 sugar units; a radical —CO—NY$_1$Y$_2$, wherein Y$_1$ and Y$_2$ are each independently of the other hydrogen or C$_1$–C$_4$-alkyl which is unsubstituted or substituted by hydroxy, or Y$_1$ and Y$_2$ together with the adjacent N-atom form a N-C$_1$–C$_2$-alkylpiperazino or morpholino ring; or a heterocyclic radical selected from the group consisting of N-pyrrolidonyl, 2- or 4-pyridinyl, 2-methylpyridin-5-yl, 2-, 3- oder 4-hydroxypyridinyl, N-ε-caprolactamyl, N-imidazolyl, 2-methylimidazol-1-yl, N-morpholinyl and 4-N-methylpiperazin-1-yl.

A particularly preferred group of non-ionic substituents of B or B' comprises the radicals —CONH$_2$, —CON(CH$_3$)$_2$,

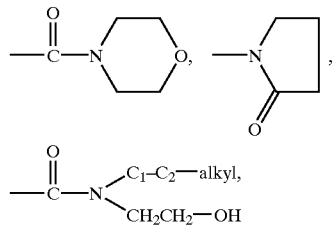

—CONH—(CH$_2$)$_2$—OH, —COO—(CH$_2$)$_2$—N(CH$_3$)$_2$, and —COO(CH$_2$)$_{2-4}$—NHC(O)—O—G wherein —O—G is the radical of trehalose.

(ii) Anionic Substituents:

Preferred anionic substituents of B or B' are C$_1$–C$_4$-alkyl, in particular C$_1$–C$_2$-alkyl, which is substituted by one or more substituents selected from the group consisting of —SO$_3$H and —OPO$_3$H$_2$, for example —CH$_2$—SO$_3$H; phenyl which is substituted by —SO$_3$H or sulfomethyl, for example o-, m- or p-sulfophenyl or o-, m- or p-sulfomethylphenyl; —COOH; a radical —COOY$_4$, wherein Y$_4$ is C$_2$–C$_6$-alkyl which is substituted by —COOH, —SO$_3$H, —OSO$_3$H, —OPO$_3$H$_2$, or by a radical —NH—C(O)—O—G' wherein G' is the radical of lactobionic acid, hyaluronic acid or sialic acid, in particular C$_2$–C$_4$-alkyl which is substituted by —SO$_3$H or —OSO$_3$H; a radical —CONY$_5$Y$_6$ wherein Y$_5$ is C$_1$–C$_6$-alkyl substituted by sulfo, in particular C$_2$–C$_4$-alkyl substituted by sulfo, and Y$_6$ is hydrogen, for example the radical —C(O)—NH—C(CH$_3$)$_2$—CH$_2$—SO$_3$H; or —SO$_3$H; or a suitable salt thereof. Particular preferred anionic substituents of B or B' are —COOH, —SO$_3$H, o-, m- or p-sulfophenyl, o-, m- or p-sulfomethylphenyl or a radical —CONY$_5$Y$_6$ wherein Y$_5$ is C$_2$–C$_4$-alkyl substituted by sulfo, and Y$_6$ is hydrogen.

(iii) Cationic Substituents:

Preferred cationic substituents of B or B' are C$_1$–C$_4$-alkyl, in particular C$_1$–C$_2$-alkyl, which is in each case substituted by —NR$_{23}$R$_{23}$'R$_{23}$''$^+$An$^-$; or a radical —C(O)OY$_7$ wherein Y$_7$ is C$_2$–C$_6$-alkyl, in particular C$_2$–C$_4$-alkyl, which is in each case substituted by —NR$_{23}$R$_{23}$'R$_{23}$''$^{+An-}$ and is further unsubstituted or substituted by hydroxy. R$_{23}$, R$_{23}$' and R$_{23}$'' are each independently of another preferably hydrogen or C$_1$–C$_4$-alkyl, more preferably methyl or ethyl and particularly preferably methyl. Examples of suitable anions An$^-$ are Hal$^-$, wherein Hal is halogen, for example Br$^-$, F$_-$, J$^-$ or particularly Cl$^-$, furthermore HCO$_3^-$, CO$_3^{2-}$, H$_2$PO$_3^-$, HPO$_3^{2-}$, PO$_3^{3-}$, HSO$_4^-$, SO$_4^{2-}$ or the radical of an organic acid such as OCOCH$_3^-$ and the like. A particularly preferred cationic substituent of B or B' is a radical —C(O)OY$_7$ wherein Y$_7$ is C$_2$–C$_4$-alkyl, which is substituted by —N(C$_1$–C$_2$-alkyl)$_3^+$An$^-$ and is further substituted by hydroxy, and An is an anion, for example the radical —C(O)O—CH$_2$—CH(OH)—CH$_2$—N(CH$_3$)$_3^+$An$^-$.

(iv) zwitterionic substituents —R$_{24}$—Zw:

R$_{24}$ is a preferably a carbonyl, ester or amide functional group and more preferably an ester group —C(O)—O—.

Suitable anionic groups of the moiety Zw are for example —COO$^-$, —SO$_3^-$, —OSO$_3^-$, —OPO$_3$H$^-$ or bivalent —O—PO$_2^-$ or —O—PO$_2^-$—O—, preferably a group —COO$^-$ or —SO$_3^-$ or a bivalent group —O—PO$_2^-$, and in particular a group —SO$_3^-$. Suitable cationic groups of the moiety Zw are for example a group —NR$_{23}$R$_{23}$'R$_{23}$''$^+$ or a bivalent group —NR$_{23}$R$_{23}$'$^+$—, wherein R$_{23}$, R$_{23}$' and R$_{23}$'' are as defined above, and are each independently of the other, preferably hydrogen or C$_1$–C$_6$-alkyl, preferably hydrogen or C$_1$–C$_4$-alkyl and most preferably each methyl or ethyl.

The moiety Zw is for example C$_2$–C$_{30}$-alkyl, preferably C$_2$–C$_{12}$-alkyl, and more preferably C$_3$–C$_8$-alkyl, which is in each case uninterrupted or interrupted by —O— and substituted or interrupted by one of the above-mentioned anionic and cationic groups each, and, in addition, is further unsubstituted or substituted by a radical —OY$_8$, wherein Y$_8$ is hydrogen or the acyl radical of a carboxylic acid.

Y$_8$ is preferably hydrogen or the acyl radical of a higher fatty acid.

Zw is preferably C$_2$–C$_{12}$-alkyl and even more preferably C$_3$–C$_8$-alkyl which is substituted or interrupted by one of the above-mentioned anionic and cationic groups each, and in addition may be further substituted by a radical —OY$_8$.

A preferred group of zwitter-ionic substituents —R$_{24}$—Zw corresponds to the formula

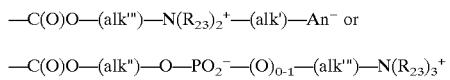

wherein R$_{23}$ is hydrogen or C$_1$–C$_6$-alkyl; An$^-$ is an anionic group —COO$^-$, —SO$_3^-$, —OSO$_3^-$ or —OPO$_3$H$^-$, preferably —COO$^-$ or —SO$_3^-$ and most preferably —SO$_3^-$, alk' is C$_1$–C$_{12}$-alkylene, (alk") is C$_2$–C$_{24}$-alkylene which is unsubstituted or substituted by a radical —OY$_8$, Y$_8$ is hydrogen or the acyl radical of a carboxylic acid, and (alk''') is C$_2$–C$_8$-alkylene.

(alk') is preferably C$_2$–C$_8$-alkylene, more preferably C$_2$–C$_6$-alkylene and most preferably C$_2$–C$_4$-alkylene. (alk") is preferably C$_2$–C$_{12}$-alkylene, more preferably C$_2$–C$_6$-alkylene and particularly preferably C$_2$–C$_3$-alkylene which is in each case unsubstituted or substituted by hydroxy or by a radical —OY$_8$. (alk''') is preferably C$_2$–C$_4$-alkylene and more preferably C$_2$–C$_3$-alkylene. R$_9$ is hydrogen or C$_1$–C$_4$-alkyl, more preferably methyl or ethyl and particularly preferably methyl. A preferred zwitterionic substituent of B or B' is of formula

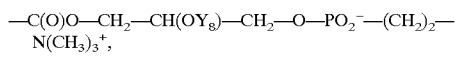

wherein Y$_8$ is hydrogen or the acyl radical of a higher fatty acid.

B denotes for example a radical of formula

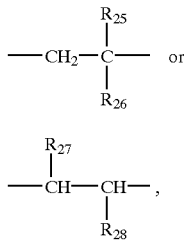

wherein R$_{25}$ is hydrogen or C$_1$–C$_4$-alkyl, preferably hydrogen or methyl; R$_{26}$ is a hydrophilic substituent, wherein the above given meanings and preferences apply; R$_{27}$ is C$_1$–C$_4$-alkyl, phenyl or a radical —C(O)OY$_9$, wherein Y$_9$ is hydrogen or unsubstituted or hydroxy-substituted C$_1$–C$_4$-alkyl; and R$_{28}$ is a radical —C(O)Y$_9$' or —CH$_2$—C(O)OY$_9$' wherein Y$_9$' independently has the meaning of Y$_9$.

R$_{27}$ is preferably C$_1$–C$_2$-alkyl, phenyl or a group —C(O)OY$_9$. R$_{28}$ is preferably a group —C(O)OY$_9$' or —CH$_2$—C(O)OY$_9$' wherein Y$_9$ and Y$_9$' are each independently of the other hydrogen, C$_1$–C$_2$-alkyl or hydroxy-C$_1$–C$_2$-alkyl. Particularly preferred —CHR$_{27}$—CHR$_{28}$— units according to the invention are those wherein R$_{27}$ is methyl or a group —C(O)OY$_9$ and R$_{28}$ is a group —C(O)OY$_9$' or —CH$_2$—C(O)OY$_9$' wherein Y$_9$ and Y$_9$' are each hydrogen, C$_1$–C$_2$-alkyl or hydroxy-C$_1$–C$_2$-alkyl.

B' independently may have one of the meanings given above for B.

If (oligomer) is a radical of formula (6a), the radical -(alk)-S—[B]$_p$—[B']$_q$—Q preferably denotes a radical of formula

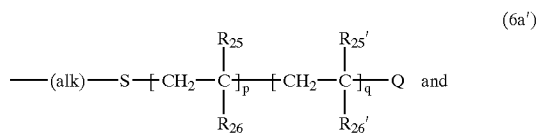

even more preferably of the formula

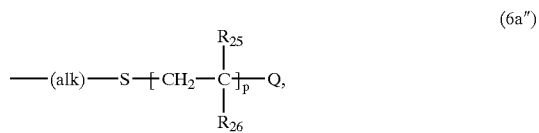

wherein for R$_{25}$, R$_{26}$, Q, p and q the above-given meanings and preferences apply, for R$_{25}$' independently the meanings and preferences given before for R$_{25}$ apply, and for R$_{26}$' independently the meanings and preferences given before for R$_{26}$ apply.

A preferred group of suitable hydrophilic macromonomers according to step (b) of the invention comprises compounds of formula

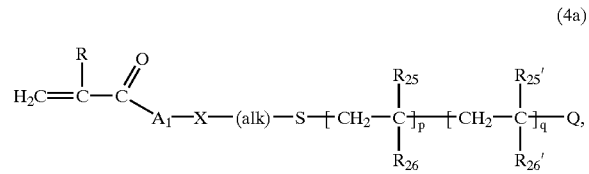

wherein R is hydrogen or methyl, A$_1$ is —O—(CH$_2$)$_{2-4}$—, —O—CH$_2$—CH(OH)—CH$_2$— or a radical —O—(CH$_2$)$_{2-4}$—NH—C(O)—, X is —O— or —NH—, (alk) is C$_2$–C$_4$-alkylene, Q is a monovalent group that is suitable to act as a polymerization chain-reaction terminator, p is an integer from 5 to 50, R$_{25}$ and R$_{25}$' are each independently of the other hydrogen or methyl, and for R$_{26}$ and R$_{26}$' each independently the above given meanings and preferences apply.

A particularly preferred embodiment of the invention relates to hydrophilic macromonomers of the formula

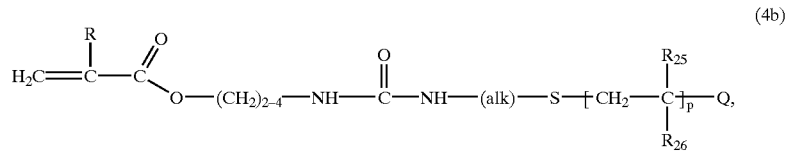

wherein for R, R$_{25}$, R$_{26}$, Q, (alk) and p the above-given meanings and preferences apply. A particularly preferred group of hydrophilic macromonomers are compounds of the above formula (4b) wherein R is hydrogen or methyl, (alk) is $C_2$–$C_4$-alkylene, $R_{25}$ is hydrogen or methyl, p is an integer of 5 to 50, Q is as defined before, and for $R_{26}$ the above given meanings and preferences apply; in particular $R_{26}$ of this embodiment is a radical —$CONH_2$, —$CON(CH_3)_2$ or

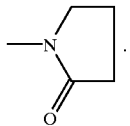

If (oligomer) is a radical (ii) of formula (6b), Q' in formula (6b) is for example $C_1$–$C_{12}$-alkyl, phenyl or benzyl, preferably $C_1$–$C_2$-alkyl or benzyl and in particular methyl. $R_{19}$ is preferably unsubstituted or hydroxy-substituted $C_1$–$C_4$-alkyl and in particular methyl. u is preferably an integer from 2 to 150, more preferably from 5 to 100, even more preferably from 5 to 75 and particularly preferably from 10 to 50.

If (oligomer) is a radical of formula (6b'), the above given meanings and preferences apply for the variables $R_{19}$ and u contained therein. X in formula (6b') is preferably hydroxy or amino.

If (oligomer) denotes a radical (iv) of formula (6c), $R_{20}$ and $R_{20}'$ are each preferably ethyl or in particular methyl; v is preferably an integer from 2 to 150, more preferably from 5 to 100, even more preferably from 5 to 75 and particularly preferably from 10 to 50; Q" is for example hydrogen; and $An^-$ is as defined before.

If (oligomer) denotes an oligopeptide radical (v) of formula (6d) or 6d'), $R_{21}$ is for example hydrogen, methyl, hydroxymethyl, carboxymethyl, 1-hydroxyethyl, 2-carboxyethyl, isopropyl, n-, sec. or iso-butyl, 4-amino-n-butyl, benzyl, p-hydroxybenzyl, imidazolylmethyl, indolylmethyl or a radical —$(CH_2)_3$—NH—C(=NH)—$NH_2$. t is preferably an integer from 2 to 150, more preferably from 5 to 100, even more preferably from 5 to 75 and particularly preferably from 10 to 50.

If (oligomer) denotes a polyoxyalkylene radical (vi) of formula (6e), $R_{34}$ is preferably hydrogen or $C_1$–$C_{18}$-alkyl, more preferably hydrogen or $C_1$–$C_{12}$-alkyl, even more preferably hydrogen, methyl or ethyl, and particularly preferably hydrogen or methyl. (alk") is preferably a $C_2$–$C_3$-alkylene radical. z is preferably 0. r and s are each independently preferably an integer from 0 to 100 wherein the total of (r+s) is 5 to 100. r and s are each independently more preferably an integer from 0 to 50 wherein the total of (r+s) is 8 to 50. In a particularly preferred embodiment of the polyoxyalkylene radicals (oligomer), r is an integer from 8 to 50 and particularly 9 to 25, and s is 0.

(oligomer) as the radical of an oligosaccharide (vii) may be, for example, a di- or polysaccharide including carbohydrate containing fragments from a biopolymer. Examples are the radical of a cyclodextrin, trehalose, cellobiose, maltotriose, maltohexaose, chitohexaose or a starch, hyaluronic acid, deacetylated hyaluronic acid, chitosan, agarose, chitin 50, amylose, glucan, heparin, xylan, pectin, galactan, glycosaminoglycan, mucin, dextran, aminated dextran, cellulose, hydroxyalkylcellulose or carboxyalkylcellulose oligomer, each of which with a molecular weight average weight of, for example, up to 25000, preferably up to 10000. Preferably the oligosaccharide according to (vii) is the radical of a cyclodextrin with a maximum of 8 sugar units.

Formulae (6a), (6a') or (6e) are to be understood as a statistic description of the respective oligomeric radicals, that is to say, the orientation of the monomers and the sequence of the monomers (in case of copolymers) are not fixed in any way by said formulae. The arrangement of B and B' in formula (6a) or of the ethyleneoxide and propyleneoxide units in formula (6e) thus in each case may be random or blockwise.

The weight average molecular weight of the hydrophilic macromonomer according to step (b) depends principally on the desired properties and is for example from 300 to 25000, preferably from 300 to 12000, more preferably from 300 to 8000, even more preferably from 300 to 5000, and particularly preferably from 500 to 4000.

The macromonomers of formula (4) may be prepared by methods known per se. For example, the compounds of formula (4) wherein A is a radical of formula (5a), (5b) or (5d) are obtainable by reacting a compound of formula

wherein R, $R_{32}$ and $R_{32}'$ each have the above-given meaning and $A^*$ is, for example, a group —C(O)—$A^{}$, wherein $A^{}$ is halogen, particularly chlorine, an ester group an oxyalkylene radical comprising an epoxy group, for example the radical

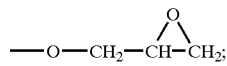

or is a radical —O—$C_2$-$C_{12}$-alkylene—N=C=O; or $A^*$ is a radical —$(A_2)$m—N=C=O, wherein $A_2$ and m have the above-given meaning, with a compound of formula

wherein X has the above-given meaning.

The reactions of a compound of formula (8) having a carboxylic acid halide group, an epoxy group or an isocyanato group with an amino or hydroxy compound of formula (9) are well-known in the art and may be carried out as desribed in textbooks of organic chemistry. For example, the reaction of an isocyanato derivative of formula (8) with a compound of formula (9) may be carried out in an inert organic solvent such as an optionally halogenated hydrocarbon, for example petroleum ether, methylcyclohexane, toluene, chloroform, methylene chloride and the like, or an ether, for example diethyl ether, tetrahydrofurane, dioxane, or a more polar solvent such as DMSO, DMA, N-methylpyrrolidone or even a lower alcohol, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. In addition, the reaction of an isocyanato derivative of formula (8) with a compound of formula (9) wherein —XH is an amino group also may be carried out in an aqueous solution in the absence of a catalyst. It is advantageous to carry out the above reactions under an inert atmosphere, for example under an nitrogen or argon atmosphere.

Moreover, the macromonomers of formula (4) wherein A is a radical of formula (5c) or (5e) may be obtained by reacting a compound of formula

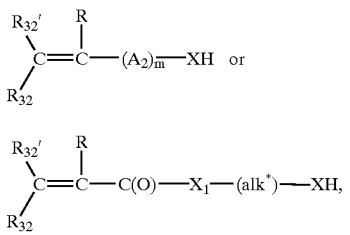
(10a)

(10b)

wherein R, $R_{32}$, $R_{32}'$, $A_2$, X, $X_1$, (alk*) and m each have the above-given meaning, with a compound of formula $$-X_1'(O)C-(oligomer) \quad (9a),$$

wherein (oligomer) has the above-given meaning and $X_1'$ is for example —OH or halogen, in particular chlorine, or together with —(O)C— forms an anhydride group, in a manner known per se.

The macromonomers of formula (4), wherein A is a direct bond and (oligomer) is a radical of formula (6c') are known or may be prepared according to methods known in the art, for example as described in S. Kobayashi et al., Polymer Bulletin 13, p 447–451 (1985).

Likewise, the macromonomers of the formula

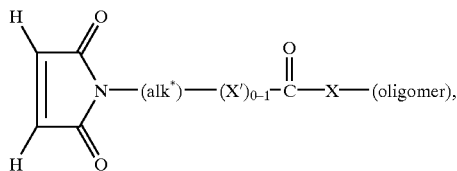
(4c)

wherein (alk*), X', X and (oligomer) each have the above-given meaning, may be obtained in a manner known per se, for example, by reacting a compound of formula

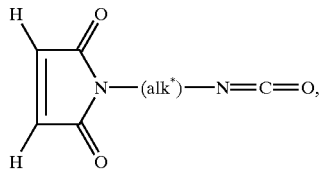
(12)

wherein (alk*) has the above-given meaning, with a compound of the above-given formula (6), or by reacting a compound of formula

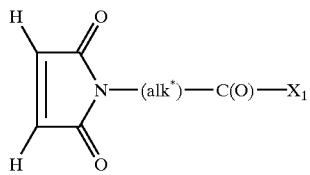
(12a)

with a compound of the above formula (9) wherein (alk*) and $X_1$ each have the above-given meaning.

The compounds of the formula (8), (9), (9a), (10a), (10b), (12) and (12a) are known compounds which are commercially available or may be prepared according to known methods. For example, compounds of the formula (9) and (9a) wherein (oligomer) denotes a radical of formula (6a) may be prepared according to PCT application WO 92/09639 by copolymerizing one or more hydrophilic ethylenically unsaturated monomers in the presence of a functional chain transfer agent such as cysteamine hydrochloride, thioglycolic acid or the like.

The hydrophilic monomers or macromonomers may be applied to the initiator-modified primary polymer coating and polymerized there according to processes known per se. For example, the material comprising the primary polymer coating is immersed in a solution of the monomer or macromonomer, or a layer of monomer or macromonomer is first of all deposited on the modified material surface, for example, by dipping, spraying, spreading, knife coating, pouring, rolling, spin coating or vacuum vapor deposition. Suitable solvents, if used in the polymerization process, are, for example, water or dipolar aprotic solvents such as, for example, acetonitrile. The polymerization of the hydrophilic monomer or macromonomer on the material comprising the primary polymer coating then may be initiated, for example, thermally by the action of heat or preferably by irradiation, particularly by UV radiation. Suitable light sources for the irradiation are known to the artisan and comprise for example mercury lamps, high pressure mercury lamps, xenon lamps, carbon arc lamps or sunlight. The time period of irradiation may depend for example on the desired properties of the resulting composite material but is usually in the range of up to 30 minutes, preferably from 10 secondes to 10 minutes, and particularly preferably from 0.5 to 5 minutes. It is advantageous to carry out the irradiation in an atmosphere of inert gas. After the polymerization, any non-covalently bound monomers, polymers, oligomers or non-reacted macromonomers formed can be removed, for example by treatment with suitable solvents.

The coated material obtained according to the invention may be purified afterwards in a manner known per se, for example by washing or extraction with a suitable solvent such as water.

According to step (b) of the above-described coating process, the brushes of the primary coating obtained according to step (a) are provided with side chains by grafting a hydrophilic monomer or macromonomer onto the primary polymer coating. The final coating typically has a so-called bottle brush-type structure (BBT) composed of tethered "hairy" chains. The BBT structure of the coatings of the invention may be varied within wide limits, for example by a suitable choice of reactive monomer, photoinitiator and chain length in step (a), or by a suitable choice of hydrophilic monomer or macromonomer and chain length in step (b). Such BBT structures in one embodiment comprise a long hydrophilic or hydrophobic backbone which carries relatively densely packed comparatively short hydrophilic side chains (called primary bottle brushes). Another embodiment relates to secondary bottle brushes which are characterized in that the hydrophilic side chains themselves carry densely packed hydrophilic "secondary" side chains. Polymeric coatings of said primary and secondary BBT structures to a certain extent mimic highly water-retaining structures occurring in the human body, for example in cartilage or mucosal tissue.

The coating thickness of the macromonomers depends principally on the desired properties. It can be, for example, from 0.001 to 1000 μm, preferably from 0.005 to 100 μm, more preferably from 0.01 to 50 μm, even more preferably from 0.01 to 5 μm, especially preferably from 0.01 to 1 μm and particularly preferably from 0.01 to 0.5 μm.

A further embodiment of the invention relates to a material that is coated by the process of the invention.

The material that is coated by the process of the invention is, for example, an organic bulk material, preferably a biomedical device, e.g. an ophthalmic device, preferably a contact lens including both hard and particularly soft contact lenses, an intraocular lens or artificial cornea. Further examples are materials useful for example as wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

The biomedical devices, e.g. ophthalmic devices obtained according to the invention have a variety of unexpected advantages over those of the prior art which make those devices very suitable for practical purposes,e.g. as contact lens for extended wear or intraocular lens. For example, they do have a high surface wettability which can be demonstrated by their contact angles, their water retention and their water-film break up time or tear film break up time (TBUT).

The TBUT plays an particularly important role in the field of ophthalmic devices such as contact lenses. Thus the facile movement of an eyelid over a contact lens has proven important for the comfort of the wearer; this sliding motion is fa cilitated by the presence of a continuous layer of tear fluid on the contact lens, a layer which lubricates the tissue/lens interface. However, clinical tests have shown that currently available contact lenses partially dry out between blinks, thus increasing friction between eyelid and the lens. The increased friction results in soreness of the eyes and reduced movement of the contact lenses. Now it has become feasible to considerably increase the TBUT of commercial contact lenses such as, for example, Focus Dailies™, Focus New Vues® or Lotrafilcon A lenses, by applying a surface coating according to the invention. On the base curve of a contact lens, the pronounced lubricity of the coating facilitates the on-eye lens movement which is essential for extended wear of contact lenses. Moreover, the materials obtained by the process of the invention provide additional effects being essential for lenses for extended wear, such as an increased thickness of the pre-lens tear film which contributes substantially to low microbial adhesion and resistance to deposit formation. Due to the extremely soft and lubricious character of the novel surface coatings, biomedical articles such as in particular contact lenses coated by the process of the invention show a superior wearing comfort including improvements with respect to late day dryness and long term (overnight) wear. The novel surface coatings moreover interact in a reversible manner with occular mucus which contributes to the improved wearing comfort.

In addition, biomedical devices, e.g. ophthalmic devices such as contact lenses, coated by the process of the invention, have a very pronounced biocompatibility combined with good mechanical properties. For example, the devices are blood compatible and have a good tissue integration. In addition, there are generally no adverse eye effects observed, while the adsorption of proteins or lipids is low, also the salt deposit formation is lower than with conventional contact lenses. Generally, there is low fouling, low microbial adhesion and low bioerosion while good mechanical properties can be for example found in a low friction coefficient and low abrasion properties. Moreover, the dimensional stability of the materials obtained according to the invention is excellent. In addition, the attachment of a hydrophilic surface coating at a given bulk material according to the invention does not affect its visual transparency.

In summary, the ophthalmic devices obtained by the process of the invention, such as contact lenses and artificial cornea, provide a combination of low spoilation with respect to cell debris, cosmetics, dust or dirt, solvent vapors or chemicals, with a high comfort for the patient wearing such opthalmic devices in view of the soft hydrogel surface which for example provides a very good on-eye movement of the ohthalmic device.

Biomedical devices such as renal dialysis membranes, blood storage bags, pacemaker leads or vascular grafts coated by the process of the invention resist fouling by proteins by virtue of the continuous layer of bound water, thus reducing the rate and extent of thrombosis. Blood-contacting devices fabricated according to the present invention are therefore haemocompatible and biocompatible.

In the examples, if not indicated otherwise, amounts are amounts by weight, temperatures are given in degrees Celsius. Tear break-up time values in general relate to the pre-lens tear film non-invasive break-up time (PLTF-NIBUT) that is determined following the procedure published by M. Guillon et al., Ophthal. Physiol. Opt. 9, 355–359 (1989) or M. Guillon et al., Optometry and Vision Science 74, 273–279 (1997). Average advancing and receding water contact angles of coated and non-coated lenses are determined with the dynamic Wilhelmy method using a Kruss K-12 instrument (Kruss GmbH, Hamburg, Germany). Wetting force on the solid is measured as the solid is immersed in or withdrawn from a liquid of known surface tension.

Surface Functionalization

EXAMPLE A-1

1,2-Diaminocyclohexane Plasma Coating (DACH)

Two dried Lotrafilcon A lenses (polysiloxane/perfluoroalkyl polyether copolymer) are, after extraction in isopropanol, toluene and again in isopropanol, placed on the glass holder within the plasma reactor equipped with an external ring electrode and a 27.13 MHz radiofrequency (RF) generator for the generation of an inductively-coupled, cold glow discharge plasma. The distance between the substrates and the lower edge of the plasma zone is 12 cm. The reactor is evacuated to a pressure of 0.008 mbar, and held at these conditions for one hour. Then, the argon plasma gas flow rate into the plasma zone of the reactor is set to 20 sccm (standard cubic centimeter), the pressure in the reactor is adjusted to 0.12 mbar and the RF generator is switched on. The plasma discharge of a power 250 Watts is maintained for a total period of 1 min (in order to clean and activate the lenses surfaces). Afterward the 1,2-DACH vapor is introduced into the reactor chamber from DACH reservoir (maintained at 24° C.) at 0.15 mbar for 1 min. After this, the following parameters for the plasma polymerization of DACH are chosen: Argon flow rate for plasma excitation=5 sccm, Argon carrier gas flow rate for DACH transport=5 sccm, temperature of the DACH evaporation unit=24° C., the distance between the lower edge of the plasma zone and the substrates=5 cm, pressure=0.2 mbar, and plasma power= 100 W. The lenses are treated for about 5 minutes with a pulsing glow discharge plasma (1 $\mu$sec. on, 3 $\mu$sec. off). After 5 minutes of deposition the plasma discharge is interrupted and DACH vapor is let to flow into reactor for other 5 min. The reactor is then evacuated and maintained for 30 minutes at a pressure 0.008 mbar in order to remove residual monomer and activated spices. The internal pressure is brought to atmospheric by using dry nitrogen. The substrates are then turned over and the whole procedure is repeated to coat the other side of the substrates. The samples are then unloaded from the reactor and used for the subsequent photoinitiator linkage.

EXAMPLE A-2

Surface Binding of a Reactive Photoinitiator

The aminofunctionalized contact lenses from Example A-1 are, immediately after plasma treatment with 1,2-DACH plasma, immersed into 1% acetonitrile solution of the reactive photoinitiator (I) prepared by the addition reaction from Isophorone diisocyanate and 4-(2-hydroxyethoxy)phenyl 2-hydroxy-2-propyl ketone (Darocure 2959) by the method described in EP 0 632 329. The amino groups on the lenses surfaces react with the isocyanato groups of the photoinitiator molecules for 12 hours. After this time, the lenses are withdrawn from the reaction solution, washed and extracted in acetonitrile for 8 hours and dried under reduced pressure for 2 hours. The dried lenses are subsequently used for photografting.

EXAMPLE A-3

Surface Binding of a Reactive Photoinitiator

The aminofunctionalized contact lenses from Example A-1 are, immediately after plasma treatment with 1,2-DACH plasma, immersed into 1% acetonitrile solution of the reactive photoinitiator (II) prepared by the addition reaction from Isophorone diisocyanate and 2-ethyl-2-(dimethylamino)-1-[4-(2-hydroxyethoxy)phenyl]-4-penten-1-one by the method described in WO 96/20796. The amino groups on the lenses surfaces react with the isocyanato groups of the photoinitiator molecules for 16 hours. After this time, the lenses are withdrawn from the reaction solution, washed and extracted in acetonitrile for 12 hours and dried under reduced pressure for 2 hours. The dried lenses are subsequently used for photografting.

EXAMPLE A-4

Surface Binding of a Thermal Polymerization Initiator 1 g of the reactive initiator 4,4'-Azobis(4-cyanovaleric acid) (ACV), 25 ml of anhydrous Acetonitrile and 0.5 g of N,N'-Dicyclohehylcarbodiimide (DCC) are charged into a 100 ml flask with a flat bottom. The mixture is stirred under nitrogen at 25° C. for 10 minutes. The aminofunctionalized contact lenses from Example A-1 are then separately immersed into the solution. The reaction between activated carboxylic groups of ACV and amino groups on lens surfaces proceeds under nitrogen at RT for 16 hours. After the reaction, the lenses are withdrawn from the reaction solution, washed and extracted in acetonitrile for 12 hours and dried under reduced pressure for 2 hours.
Photografting of Reactive Monomers

EXAMPLE B-1

Photografting of 2-Isocyanatoethyl Methacrylate (IEM) onto the Contact Lens Surface 1.0 g of IEM is dissolved in 9 ml of acetonitrile and the solution is stirred under argon flow for 5 minutes. Argon is then let to bubble through the solution for the period of about 10 minutes. The filtered solution is then filtered through 0.45 $\mu$m Teflon filter and degassed with argon for additional 10 minutes. The filtered solution is then frozen in a flask in liquid nitrogen, the flask is evacuated under a high vacuum, transferred into a glove box and used for photografting.

1 ml of the IEM solution is introduced into a small Petri dish of a volume of about 3 ml in a glow box. The dried lens from Example A-2, carrying covalently linked photoinitiator molecules on its surface, is then placed into this solution and an additional 1 ml of the degassed solution is added on the lens in order to cover the whole lens with the solution. After 5 minutes, the Petri dish with the lens in the solution is exposed to 15 mW ultraviolet light for a period of about 3 minutes. The lens is then turned over and the exposition is repeated by applying 15 mW UV light for an additional 3 minutes.

The modified lens is then withdrawn from the solution, washed twice in dried acetonitrile, continuously extracted and dried acetonitrile for 2 h.

EXAMPLE B-2

Photografting of 2-Vinyl-4,4-dimethyl Azlactone (VAL) onto the Contact Lens Surface 1.5 g of VAL are dissolved in 13.5 ml of acetonitrile and the solution is stirred under argon flow for 5 minutes. Argon is then let to bubble through the solution for the period of about 10 minutes. The solution is then filtered through 0.45 $\mu$m Teflon filter and degassed with argon for additional 10 minutes. The filtered solution is then frozen in a flask in liquid nitrogen, the flask is evacuated under a high vacuum, transferred into a glove box and used for photografting.

1 ml of the VAL solution is introduced into a small Petri dish of a volume of about 3 ml in a glove box. The dried lens from Example A-3, carrying covalently linked photoinitiator molecules on its surface, is then placed into this solution and an additional 1 ml of the degassed solution is added on the lens in order to cover the whole lens with the solution. After 5 minutes, the Petri dish with the lens in the solution is exposed to 15 mW ultraviolet light for a period of about 3 minutes. The lens is then turned over and the exposition was repeated by applying 15 mW UV light for an additional 3 minutes. The modified lens is then withdrawn from the solution, washed twice in dried acetonitrile and continuously extracted in dried acetonitrile for 2 h.

EXAMPLES B-3 to B-5

Photografting of Other Reactive Molecules onto the Contact Lens Surface

The following reactive monomers are photografted onto the lens surface obtained according to Example A-2 using the process described in Examples B-1 and B-2:

| Example | Monomer used |
|---------|--------------|
| B-3 | Glycidyl methacrylate |
| B-4 | Acrylic acid |
| B-5 | Acrylic acid anhydride |

EXAMPLE B6

Thermografting of a Polymerizable Photoinitiator onto the Contact Lens Surface

A 100 ml flask with a flat bottom, condenser and thermometer is charged with 1.5 g of the polymerizable photoinitiator of the formula

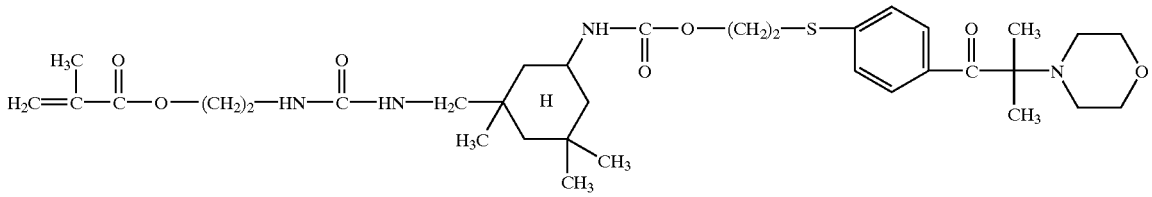

(synthesis see PCT application WO 96/20919, Example H1 on page 53) and 13.5 ml of acetonitrile and the solution is stirred under argon flow for 5 minutes. Argon is then let to bubble through the solution for the period of about 10 minutes. The solution is then filtered through 0.45 µm Teflon filter and degassed with argon for additional 10 minutes. The dried lenses from Example A-4, carrying covalently linked initiator molecules on its surface, are then placed into the solution. The whole mixture is then heated to 60° C. to start the polymerization process. Polymerization proceeds under argon flow and gentle stirring of the mixture, at 60° C. for 24 hours. The modified lenses are then withdrawn from the solution, washed twice in anhydrous acetonitrile, continuously extracted in anhydrous acetonitrile for additional 4 h and used for further modification.

Introduction of Polymerization Initiators to the Primary Polymer Coating

EXAMPLE C-1

Coupling of 4-(2-Hydroxyethoxy)phenyl 2-Hydroxy-2-propyl Ketone (Darocure 2959) to Isocyanate Groups of Poly-IEM Chains Grafted on a Lens Surface The isocyanate groups of the functionalized lens from Example B-1 are reacted with 4-(2-hydroxyethoxy)phenyl 2-hydroxy-2-propyl ketone (Darocure 2959) by immersing the lens into 3 ml acetonitrile solution containing 30 mg of Darocure 2959 and 10 µg of dibutyltin dilaurate (DBTDL) as catalyst. The reaction is carried out under argon atmosphere at 30 ° C. for 48 hours. The lens is then withdrawn from the solution, washed 2× in acetonitrile, continuously extracted in acetonitrile for 4 hours, dried and used for photografting.

EXAMPLE C-2

Coupling of δ,δ'-azo-bis(δ-cyano-n-pentanol) to Isocyanate Groups of Poly-IEM Chains Grafted on a Lens Surface The coupling of δ,δ'-azo-bis(δ-cyano-n-pentanol) to isocyanate groups of the functionalized lens from Example B-1 is done analogously to Example C-1.

Synthesis of Telomers and Macromonomers

EXAMPLE D-1

Acrylamide Telomer

A 1000 mL three-necked round bottom flask is charged with a solution of 17.5 g (154 mmol) cysteamine hydrochloride in 150 deionized water. 1.1 g (4 mmol) α,α'-azodiisobutyramidine dihydrochloride and a solution of 142 g (2 mol) acrylamide in 450 mL deionized water are added. The pH of the solution is adjusted to pH 3 by addition of 1 molar hydrochloric acid. An intensive cooler and an internal thermometer are connected to the flask. The apparatus is evacuated to 100 mbar and filled with argon. This is repeated five times. The mixture is heated to 60° C. for three hours and then cooled to room temperature. An analytical sample is freeze-dried and the monomer conversion was determined by 1H-NMR spectroscopy. No resonances corresponding to C═C double bonds can be detected, indicating >98% conversion of the monomer.

The pH of the remaining mixture is adjusted to 10.5 by addition of 1 molar sodium hydroxide solution and diluted to a total volume of 1200 mL. Salts and low molecular weight residues such as unreacted chain transfer agent are removed by reverse osmosis using a Millipore Proscale system equipped with a Millipore Helicon RO-4 Nanomax 50 membrane operating at a pressure of 15 bar. The product is isolated from the obtained retentate by freeze-drying. Yield: 102 g of a white powder.

The concentration of amino groups is determined by functional group titration, result 0.22 mmol/g NH2 corresponding to an average molecular weight of the telomer of 4500 g/mol. GPC-analysis indicate a monomodal molecular weight distribution and the absence of high molecular weight polymer.

EXAMPLE D-2

Acryloyl Morpholine Telomer

A 100 mL three-necked round bottom flask i charged with a solution of 1.6 g (14.3 mmol) cysteamine hydrochloride in 45 mL of 0.1 molar aqueous acetic acid. 55 mg (0.2 mmol) α,α'-azodiisobutyramidine dihydrochloride and 14.1 g (100 mmol) acryloyl morpholine are added. An intensive cooler and an internal thermometer are connected to the flask. The apparatus is evacuated to 100 mbar and filled with argon. This is repeated five times. The mixture is heated to 60° C. for four hours and then cooled to room temperature. An analytical sample is freeze-dried and the monomer conversion is determined by $^1$H-NMR spectroscopy. No resonances corresponding to C═C double bonds can be detected, indicating >98% conversion of the monomer.

The remaining mixture is freeze-dried, dissolved in methanol and the telomer is precipitated in 2 liters of diethyl ether and collected by filtration.

The telomer is redissolved in 50 mL water and the pH is adjusted to 10.5 by addition of 143 mL 0.1 molar sodium hydroxide solution and then diluted with water to a total volume of 500 mL. Salts and residual low molecular weight components are removed by ultrafiltration using a UFP-1-E-4A cartridge from A/G Technology Corporation, Needham, Mass. The concentration of amino-groups is determined by functional group titration, result 0.54 mmol/g NH$_2$ corresponding to an average molecular weight of the telomer of 1850 g/mol.

EXAMPLE D-3

Telomer from α,α'-mono- Isocyanatoethyl Methacrylato Trehalose

A 100 mL three-necked round bottom flask is charged with a solution of 3.8 g (33.4 mmol) cysteamine hydrochloride in 45 mL of 0.1 molar aqueous acetic acid. 55 mg (0.2 mmol) α,α'-azodiisobutyramidine dihydrochloride and 53 g (106 mmol) mono-isocyanatoethyl methacrylato trehalose are added. An intensive cooler and an internal thermometer are connected to the flask. The apparatus is evacuated to 100 mbar and filled with argon. This is repeated five times. The mixture is heated overnight to 60° C. and then cooled to room temperature. The product precipitates in 2 liters of acetone and is isolated by filtration, yielding a slightly yellow colored powder. No resonances corresponding to C=C double bonds can be detected by $^1$H-NMR spectroscopy, indicating >98% conversion of the monomer.

The product is dissolved in 200 mL water and the pH is adjusted to 10.5 by addition of 107 mL 0.1 molar sodium hydroxide solution and then diluted with water to a total volume of 500 mL. Salts and residual low molecular weight components are removed by ultrafiltration using a UFP-1-E-4A cartridge from A/G Technology Corporation, Needham, Mass. The concentration of amino-groups is determined by functional group titration, result 0.12 mmovg $NH_2$ corresponding to an average molecular weight of the telomer of 8300 g/mol and a degree of polymerization of 16.

EXAMPLE D-4

Co-telomerization of Hydroxyethyl Acrylamide and N-acryloyl Morpholine

A 1000 mL three-necked round bottom flask is charged with a solution of 28.4 g (250 mmol) cysteamine hydrochloride in 400 mL deionized water. 407 mg (1.5 mmol) α,α'-azodiiso-butyramidine dihydrochloride and 70.6 g (500 mmol) acryloyl morpholine and 28.8 g (250 mmol) N-hydroxyethyl acrylamide are added. An intensive cooler and an internal thermometer are connected to the flask. The apparatus is evacuated to 100 mbar and filled with argon. This is repeated five times. The mixture is heated to 60° C. for four hours and then cooled to room temperature. An analytical sample is freeze-dried and the monomer conversion is determined by $^1$H-NMR spectroscopy. No resonances corresponding to C=C double bonds can be detected, indicating >98% conversion of the monomer. The remaining mixture is adjusted to pH=10 by addition of 30% KOH solution. Salts and low molecular weight residues such as unreacted chain transfer agent are removed by reverse osmosis using a Millipore Proscale system equipped with a Millipore Helicon RO-4 Nanomax 50 membrane operating at a pressure of 15 bar. The product is isolated from the obtained retentate by freeze-drying.

The concentration of amino-groups is determined by functional group titration, result 0.95 mmol/g $NH_2$ corresponding to an average molecular weight of the co-telomer of 1050 g/mol. GPC-analysis indicates a monomodal molecular weight distribution and the absence of high molecular weight polymer.

EXAMPLE D-5

Acrylamide Telomer

A 1000 mL round bottom flask is charged with a solution of 71.1 g (1 mol) acrylamide, 4.93 g (18.2 mmol) α,α'-azodiisobutyramidine dihydrochloride and 4.93 g (36.4 mmol) Cysteaminhydrochloride in 400 mL of water. The clear and slightly yellowish solution is acidified with a few drops of Hydrochloric Acid to pH3. The stirred acidic solution is evacuated to 50 mbar and filled with argon. This is repeated three times. With a constant stream of Argon, this solution is poured into a 500 ml dropping funnel which was put onto a 'flow-through-reactor' consisting of a 100 mL three-necked round-bottom flask, reflux condenser, thermometer, magnetic stirrer and a 30 cm Liebig-condenser, which is filled with glass wool. The whole apparatus is constantly purged with Argon.

The dropping funnel is put onto the Liebig condenser, which is heated to 65° C. The flask is heated to 60° C. Slowly the solution is dropped through the Liebig-condenser into the stirred flask. This takes 2.5 hrs in which the temperature in the flask is kept between 58–65° C. After the completion of the addition, the solution is stirred for 2 hrs at 60° C. NaOH is added to the clear and slightly yellowish solution until pH10 is reached. The product is cleaned through reverse osmosis, using Millipore cartridge with a cut-off at 1000 Da and freeze-dried. A bright-white solid product is obtained. The concentration of amino groups is determined via functional group titration (0.34 mEq/g) which corresponds well with the sulfur-value of the elemental analysis (0.33 mEq/g). $M_n$ 2000 g/Mol.

EXAMPLE D-6

Preparation of an Acrylamide Macromonomer 6.5 g of the acrylamide telomer with an amino end group (amine titration=0.22 mEq/g), prepared according to Example D-1 are dissolved in 80 ml of 0.15 M aqueous NaCl. Argon is then let to bubble through the solution for the period of about 30 minutes. This mixture is then added to the equimolar amount (0.2 g) of isocyanatoethyl methacrylate (IEM, isocyanate titration=6.45 mEq/g) under stirring. The whole mixture is then stirred under argon flow for 4 hours. The mixture is then filtered through 0.45 µm Teflon filter, degassed with argon in order to remove oxygen and used for photografting.

EXAMPLE D-7

Preparation of an Acryloylmorpholine Macromonomer 6.2 g of the acryloylmorpholine telomer with an amino end group (amine titration=0.54 mEq/g), prepared according to Example D-2 are dissolved in 80 ml of HPLC water. Argon is then let to bubble through the solution for the period of about 30 minutes. This mixture is then added to the equimolar amount (0.52 g) of isocyanatoethyl methacrylate (IEM, isocyanate titration=6.45 mEq/g) under stirring. The whole mixture is then stirred under argon flow for 4 hours. The mixture is then filtered through 0.45 µTeflon filter, degassed with argon in order to remove oxygen and used for photografting.

EXAMPLE D-8

Preparation of a Trehalose Macromonomer 6.45 g of 6-O-carbamoylmethacryloylethyl-α,α'-trehalose telomer with an amino end group (amine titration= 0.12 mEq/g), prepared according to Example D-3 are dissolved in 80 ml of HPLC water. The solution is then degassed by bubbling nitrogen through the solution for 30 minutes. This solution is then added to the equimolar amount (0.12 g) of isocyanatoethyl methacrylate (IEM, isocyanate titration=6.45 mEq/g) under stirring. The whole mixture is then stirred under argon flow for 4 hours. The mixture is then filtered through 0.45 µm Teflon filter, degassed with argon in order to remove oxygen and used for photografting.

Synthesis of Bottle-brush Type Coatings on a Material Surface

EXAMPLE E-1

Photografting of an Acrylamide Macromonomer onto the Contact Lens Surface 1 ml of the acrylamide macromonomer solution from Example D-6 is introduced into a small -Petri dish of a volume of about 3 ml in a glove box. The dried lens from Example C-1, carrying covalently linked photoinitiator molecules on its surface, is then placed into this solution and an additional 1 ml of the degassed solution is added on the lens in order to cover the whole lens with the solution. After 15 minutes, the Petri dish with the lens in the solution is exposed to 15 mW ultraviolet light for a period of about 3 minutes. The lens is then turned over and the exposition is repeated by applying 15 mW UV light for an additional 3 minutes.

The modified lens is then withdrawn from the solution, washed twice in destined water, continuously extracted in ultra pure water for 16 h and analyzed by ATR-FTIR and contact angle measurements.

ATR-FTIR confirms a polyacrylamide-like structure of the coating. Water/air contact angles on the modified lens are 0° adv., 0° rec., 0° hysteresis. In comparison, the contact angles of non-modified lens are 1010 adv., 640 rec., 370 hysteresis.

EXAMPLE E-2

Photografting of an Acrylamide Macromonomer onto the Contact Lens Surface

Two lenses from Example C-1 are coated in accordance with Example E-1, but instead of 3 minutes of exposition, 2 minutes exposition time are used for photografting. Water/air contact angles on the modified lenses are 52° adv., 36° rec., 16° hysteresis.

EXAMPLE E-3

Photografting of an Acryloylmorpholine Macromonomer onto the Contact Lens Surface 1 ml of the acryloylmorpholine macromonomer solution from Example D-7 are introduced into a small Petri dish of a volume of about 3 ml in a glow box. The dried lens from Example C-1, carrying covalently linked photoinitiator molecules on its surface, is then placed into this solution and an additional 1 ml of the degassed solution are added on the lens in order to cover the whole lens with the solution. After 15 minutes, the Petri dish with the lens in the solution is exposed to 15 mW ultraviolet light for a period of about 3.5 minutes. The lens is then turned over and the exposition is repeated by applying 15 mW UV light for an additional 3.5 minutes.

The modified lens is then withdrawn from the solution, washed twice in destined water, continuously extracted in ultra pure water for 16 h and analyzed by contact angle measurements.

Water/air contact angles on the modified lens are 67° adv., 39° rec., 28° hysteresis. In comparison, the contact angles of the non-modified lens are 101° adv., 64° rec., 37° hysteresis.

EXAMPLE E-4

Photografting of a Trehalose Macromonomer onto the Contact Lens Surface 1 ml of the trehalose macromonomer solution from Example D-8 is introduced into a small Petri dish of a volume of about 3 ml in a glow box. The dried lens from Example C-1, carrying covalently linked photoinitiator molecules on its surface, is then placed into this solution and an additional 1 ml of the degassed solution are added on the lens in order to cover the whole lens with the solution. After 15 minutes, the Petri dish with the lens in the solution is exposed to 15 mW ultraviolet light for a period of about 3.5 minutes. The lens is then turned over and the exposition is repeated by applying 15 mW UV light for an additional 3.5 minutes.

The modified lens is then withdrawn from the solution, washed twice in destined water, continuously extracted in ultra pure water for 16 h and analyzed by contact angle measurements.

Water/air contact angles on the modified lens are 45° adv., 30° rec., 15° hysteresis. In comparison, the contact angles of the non-modified lens are 101° adv., 64° rec., 37° hysteresis.

EXAMPLE E-5

Photografting of N-vinyl-2-pyrrolidone (NVP) onto the Contact Lens Surface 2.0 g of NVP are dissolved in 18 ml water and the solution is stirred under argon flow for 5 minutes. Argon is then let to bubble through the solution for the period of about 10 minutes. The solution is then filtered through 0.45 $\mu$m Teflon filter and degassed with argon for additional 10 minutes. The filtered solution is then frozen in a flask in liquid nitrogen, the flask evacuated under a high vacuum, transferred into a glove box and used for photografting.

1 ml of the aqueous NVP solution are introduced into a small Petri dish of a volume of about 3 ml in a glove box. The dried lens from Example C-1, carrying covalently linked photoinitiator molecules on its surface, is then placed into this solution and an additional 1 ml of the degassed solution is added on the lens in order to cover the whole lens with the solution. After 5 minutes, the Petri dish with the lens in the solution is exposed to 15 mW ultraviolet light for a period of about 3 minutes. The lens is then turned over and the exposition is repeated by applying 15 mW UV light for an additional 3 minutes. The modified lens is then withdrawn from the solution, washed twice in HPLC water, continuously extracted in ultra pure water for 16 h and analyzed by contact angle measurements.

Water/air contact angles on the modified lens are 29° adv., 19° rec., 11° hysteresis. In comparison, the contact angles of non-modified lens are 101° adv., 64° rec., 37° hysteresis.

EXAMPLE E-6

Photografting of an Acrylamide Macromonomer onto the Contact Lens Surface 1 ml of the acrylamide macromonomer solution from Example D-6 is introduced into a small Petri dish of a volume of about 3 ml in a glove box. The dried lens from Example B-6, carrying covalently linked photoinitiator molecules on its surface, is then placed into this solution and an additional 1 ml of the degassed solution is added on the lens in order to cover the whole lens with the solution. After 15 minutes, the Petri dish with the lens in the solution is exposed to 15 mW ultraviolet light for a period of about 3 minutes. The lens is then turned over and the exposition is repeated by applying 15 mW UV light for an additional 3 minutes.

The modified lens is then withdrawn from the solution, washed twice in destined water, continuously extracted in ultra pure water for 16 h and analyzed by ATR-FTIR and contact angle measurements.

ATR-FTIR confirms a polyacrylamide-like structure of the coating. Water/air contact angles on the modified lens are 44° adv., 28° rec., 16° hysteresis. In comparison, the contact angles of the non-modified lens are 101° adv., 64° rec., 37° hysteresis.

EXAMPLE E-7

Photografting of Acrylamide Monomers (AAm) onto the Contact Lens Surface 2.0 g of AAm are dissolved in 18 ml water and the solution is stirred under argon flow for 5 minutes. Argon is then let to bubble through the solution for the period of about 10 minutes. The solution is then filtered through 0.45 μm Teflon filter and degassed with argon for additional 10 minutes. The filtered solution is then frozen in a flask in liquid nitrogen, the flask is evacuated under a high vacuum, transferred into a glove box and used for photografting.

1 ml of the aqueous AAm solution are introduced into a small Petri dish of a volume of about 3 ml in a glove box. The dried lens from Example B-6, carrying covalently linked photoinitiator molecules on its surface, is then placed into this solution and an additional 1 ml of the degassed solution are added on the lens in order to cover the whole lens with the solution. After 5 minutes, the Petri dish with the lens in the solution is exposed to 15 mW ultraviolet light for a period of about 3 minutes. The lens is then turned over and the exposition was repeated by applying 15 mW UV light for an additional 3 minutes. The modified lens is then withdrawn from the solution, washed twice in HPLC water, continuously extracted in ultra pure water for 16 h and analyzed by contact angle measurements.

Water/air contact angles on the modified lens are 39° adv., 19° rec., 20° hysteresis. In comparison, the contact angles of the non-modified lens are 101° adv., 64° rec., 37° hysteresis.

What is claimed is:

1. A process for coating a material surface, comprising the steps of:
   (a) providing the material surface with polymer brushes comprising polymerization initiator radicals; and
   (b) graft polymerizing one or more different ethylenically unsaturated hydrophilic monomers or macromonomers onto the polymerization initiator-modified polymer brushes.

2. A process according to claim 1, wherein the polymer brushes according to step (a) are provided by
   (a1) covalently binding a polymerization initiator to the surface;
   (a2) graft polymerizing a vinyl monomer carrying a reactive group onto the initiator-modified material surface and thereby providing the surface with polymer brushes comprising reactive groups; and
   (a3) reacting the reactive groups of the polymer brushes with a reactive polymerization initiator having a functional group that is coreactive with the reactive groups of the polymer brushes.

3. A process according to claim 2, wherein the vinyl monomer according to step (a2) is an ethylenically unsaturated compound having from 2 to 18 C-atoms which is substituted by a reactive group selected from the group consisting of a hydroxy, amino, carboxy, carboxylic acid ester, carboxylic acid anhydride, epoxy, lactone, azlactone and isocyanato group.

4. A process according to claim 2, wherein the vinyl monomer of step (a2) is of formula

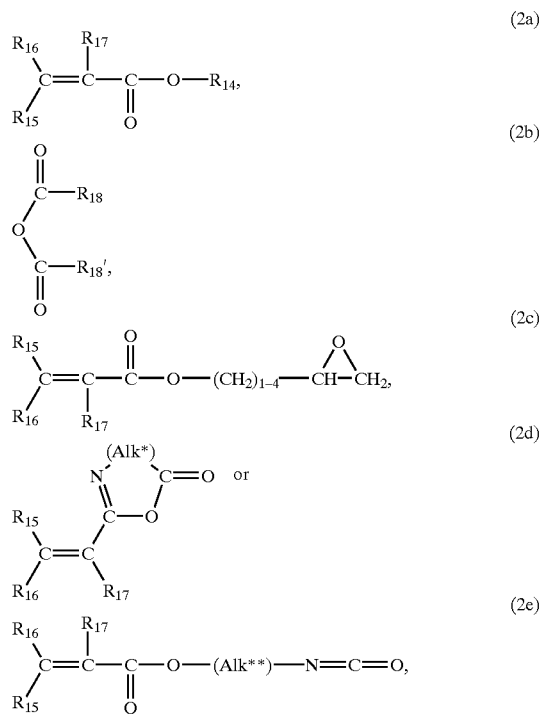

wherein $R_{14}$ is hydrogen, unsubstituted or hxdroxy-substituted $C_1$–$C_6$-alkyl or phenyl, $R_{15}$, and $R_{16}$ each independently of the other is hydrogen, $C_1$–$C_4$-alkyl, phenyl, carboxy or halogen, $R_{17}$ is hydrogen, $C_1$–$C_4$-alkyl or halogen, $R_{18}$ and $R_{18}'$ are each an ethylenically unsaturated radical having from 2 to 6 C-atoms, or $R_{18}$ and $R_{18}'$ together form a bivalent radical —$C(R_{15})$=$C(R_{17})$— wherein $R_{15}$ and $R_{17}$ are as defined above, and (Alk*) is $C_1$–$C_6$-alkylene, and (Alk**) is $C_2$–$C_{12}$-alkylene.

5. A process according to claim 2, wherein the reactive polymerization initiator of step (a3) is of formula

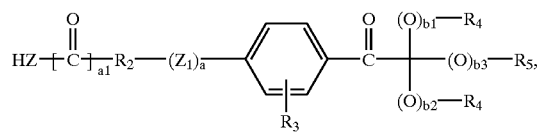

wherein Z is bivalent —O—, —NH— or —$NR_{12}$ and $R_{12}$ is linear or branched $C_1$–$C_6$-alkyl;

a1 is an integer of 0 or 1;

$R_2$ is a direct bond or linear or branched $C_1$–$C_8$-alkylene that is unsubstituted or substituted by -OH and/or is uninterrupted or interrupted by one or more groups —O—, —O—C(O)— or —O—C(O)—O—;

$R_3$ is H, $C_1$–$C_{12}$-alkyl, $C_1$–$C_{12}$-alkoxy, N-$C_1$–$C_{12}$-alkylamino or N,N-di-$C_1$–$C_{12}$-alkylamino;

$R_4$ and $R_5$ are each independently of the other H, linear or branched $C_1$–$C_8$-alkyl, $C_1$–$C_8$-hydroxyalkyl or $C_6$–$C_{10}$-aryl, or the groups $R_4$—$(O)_{b1}$— and $R_4$—$(O)_{b2}$— together are —$(CH_2)_c$— wherein c is an integer from 3 to 5, or the groups $R_4$—$(O)_{b1}$—, $R_4$—$(O)_{b2}$— and $R_5$—$(O_1)_{b3}$— together are a radical of the formula

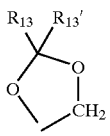

wherein $R_{13}$ and $R_{13}'$ are each independently of the other H, $C_1$–$C_8$-alkyl, $C_3$–$C_8$-cycloalkyl, benzyl or phenyl;

Z, is —O—, —O—(O)C—, —C(O)—O— or —O—C(O)—O—; and a, b1, b2 and b3 are each independently of the other 0 or 1;

subject to the provisos that b1 and b2 are each 0 when $R_5$ is H; that the total of (b1+b2+b3) is not exceeding 2; and that a is 0 when $R_2$ is a direct bond.

6. A process according to claim 1, wherein in step (a) the surface already comprises or is provided with H-active groups that are coreactive with isocyanato groups, and said H-active groups are reacted with a polymerization initiator of formula

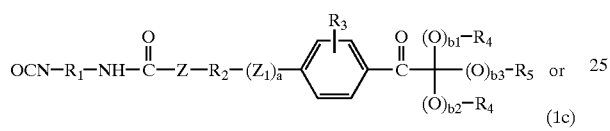

(1b)

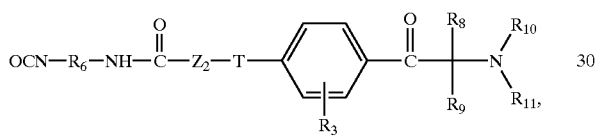

(1c)

wherein $R_1$ is branched $C_3$–$C_{18}$-alkylene, unsubstituted or $C_1$–$C_4$-alkyl- or $C_1$–$C_4$-alkoxy-substituted $C_6$–$C_{10}$-arylene, or unsubstituted or $C_1$–$C_4$-alkyl- or $C_1$–$C_4$-alkoxy-substituted $C_7$–$C_{18}$-aralkylene, unsubstituted or $C_1$–$C_4$-alkyl- or $C_1$–$C_4$-alkoxy-substituted $C_3$–$C_8$-cycloalkylene, unsubstituted or $C_1$–$C_4$-alkyl- or $C_1$–$C_4$-alkoxy-substituted $C_3$–$C_8$-cycloalkylene-$C_yH_{2y}$— or unsubstituted or $C_1$–$C_4$-alkyl- or $C_1$–$C_4$-alkoxy-substituted —$C_yH_{2y}$($C_3$–$C_8$-cycloalkylene)-$C_yH_{2y}$— wherein y is an integer from 1 to 6;

$R_2$ is a direct bond or linear or branched $C_1$–$C_8$-alkylene that is unsubstituted or substituted by —OH and/or is uninterrupted or interrupted by one or more groups —O—, —O—C(O)— or —O—C(O)—O—;

$R_3$ is H, $C_1$–$C_{12}$-alkyl, $C_1$–$C_{12}$-alkoxy, N—$C_1$–$C_{12}$-alkylamino or N,N-di-$C_1$–$C_{12}$-alkylamino;

$R_4$ and $R_5$ are each independently of the other H, linear or branched $C_1$–$C_8$-alkyl, $C_1$–$C_8$-hydroxyalkyl or $C_6$–$C_{10}$-aryl, or the groups $R_4$—(O)$_{b1}$— and $R_4$—(O)$_{b2}$— together are —(CH$_2$)$_c$— wherein c is an integer from 3 to 5, or the groups $R_4$—(O)$_{b1}$—, $R_4$—(O)$_{b2}$— and $R_5$—(O$_1$)$_{b3}$— together are a radical of the formula

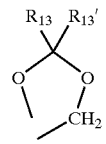

wherein $R_{13}$ and $R_{13}'$ are each independently of the other H, $C_1$–$C_8$-alkyl, $C_3$–$C_8$-cycloalkyl, benzyl or phenyl;

Z is bivalent —O—, —NH— or —NR$_{12}$—, wherein $R_{12}$ is linear or branched $C_1$–$C_6$-alkyl;

$Z_1$ is —O—, —O—(O)C—, —C(O)—O— or —O—C(O)—O—;

a, b1, b2 and b3 are each independently of the other 0 or 1;

$R_6$ independently has the same definitions as $R_1$ or is linear $C_3$–$C_{18}$-alkylene;

$Z_2$ is a direct bond or —O—(CH$_2$)$_d$— wherein d is an integer from 1 to 6 and the terminal CH$_2$ group of which is linked to the adjacent T in formula (10c);

T is bivalent —O—, —NH—, —S—, $C_1$-$C_8$-alkylene or

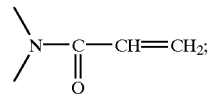

$R_8$ is linear or branched $C_1$–$C_8$-alkyl, $C_2$–$C_8$-alkenyl or $C_6$–$C_{10}$-aryl-$C_1$–$C_8$-alkyl;

$R_9$ independently of $R_8$ has the same definitions as $R_8$ or is $C_6$–$C_{10}$-aryl, or $R_8$ and $R_9$ together are —(CH$_2$)$_e$— wherein e is an integer from 2 to 6;

$R_{10}$ and $R_{11}$ are each independently of the other linear or branched $C_1$–$C_8$-alkyl that may be substituted by $C_1$–$C_4$-alkoxy, or $C_6$–$C_{10}$-aryl-$C_1$–$C_8$-alkyl or $C_2$–$C_8$-alkenyl; or $R_{10}$ and $R_{11}$ together are —(CH$_2$)$_{f1}$—$Z_3$—(CH$_2$)$_{f2}$— wherein $Z_3$ is a direct bond, —O—, —S— or —NR$_7$—, and $R_7$ is H or $C_1$–$C_8$-alkyl and f1 and f2 are each independently of the other an integer from 2 to 4;

subject to the provisos that b1 and b2 are each 0 when $R_5$ is H; that the total of (b1+b2+b3) is not exceeding 2; and that a is 0 when $R_2$ is a direct bond.

7. A process according to claim 6, wherein the surface is provided with H-active —OH, —NH$_2$ and/or —NH— groups, in some or all of them an H-atom having been substituted by a radical of formula

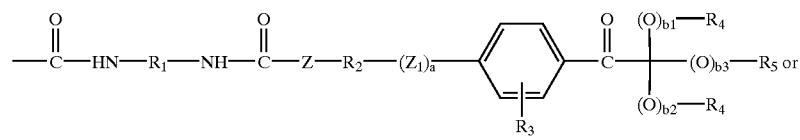

(1b')

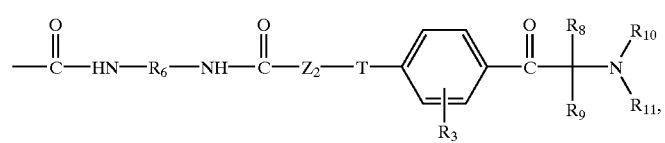

(1c')

wherein the variables $R_1$–$R_{11}$, T, Z, $Z_1$, $Z_2$, a, b1, b2 and b3 are as defined in claim 6.

8. A process according to claim 1, wherein the polymer brushes according to step (a) of the process are provided by
- (a1) covalently binding a polymerization initiator to the surface; and
- (a2') graft polymerizing an ethylenically unsaturated polymerization initiator onto the initiator-modified material surface, wherein said ethylenically unsaturated polymerization initiator is a photoinitiator in case of a thermal polymerization initiator in step (a1), or is a thermal polymerization initiator in case of a photoinitiator in step (a1).

9. A process according to claim 8, wherein the polymerization initiator of step (a1) is a thermal polymerization initiator, preferably an azo-bis($C_2$–$C_{12}$-alkane carboxylic acid) wherein the alkane moiety is in each case unsubstituted or substituted by cyano.

10. A process according to claim 8, wherein the ethylenically unsaturated polymerization initiator of step (a2') is of formula

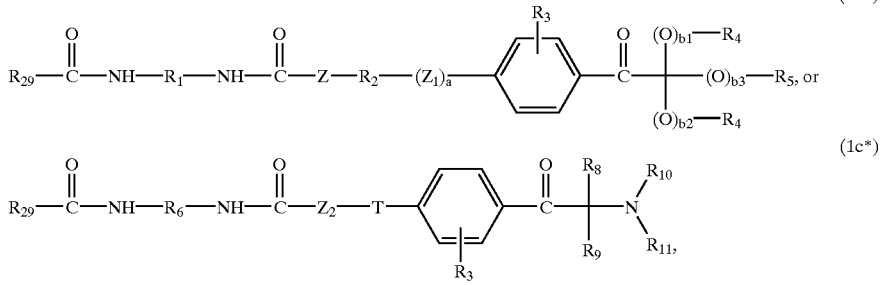

wherein $R_1$ is branched $C_3$–$C_{18}$-alkylene, unsubstituted or $C_1$–$C_4$-alkyl- or $C_1$–$C_4$-alkoxy-substituted $C_6$–$C_{10}$-arylene, or unsubstituted or $C_1$–$C_4$-alkyl- or $C_1$–$C_4$-alkoxy-substituted $C_7$–$C_{18}$-aralkylene, unsubstituted or $C_1$–$C_4$-alkyl- or $C_1$–$C_4$-alkoxy-substituted $C_3$–$C_8$-cycloalkylene, unsubstituted or $C_1$–$C_4$-alkyl- or $C_1$–$C_4$-alkoxy-substituted $C_3$–$C_8$-cycloalkylene-$C_yH_{2y}$— or unsubstituted or $C_1$–$C_4$-alkyl- or $C_1$–$C_4$-alkoxy-substituted —$C_yH_{2y}$—($C_3$–$C_8$-cycloalkylene)-$C_yH_{2y}$— wherein y is an integer from 1 to 6;

$R_2$ is a direct bond or linear or branched $C_1$–$C_8$-alkylene that is unsubstituted or substituted by —OH and/or is uninterrupted or interrupted by one or more groups —O—, —O—C(O)— or —O—C(O)—O—;

$R_3$ is H, $C_1$–$C_{12}$-alkyl, $C_1$–$C_{12}$-alkoxy, N—$C_1$–$C_{12}$-alkylamino or N,N-di-$C_1$–$C_{12}$-alkylamino;

$R_4$ and $R_5$ are each independently of the other H, linear or branched $C_1$–$C_8$-alkyl, $C_1$–$C_8$-hydroxyalkyl or $C_6$–$C_{10}$-aryl, or the groups $R_4$—$(O)_{b1}$— and $R_4$—$(O)_{b2}$— together are —$(CH_2)_c$— wherein c is an integer from 3 to 5, or the groups $R_4$—$(O)_{b1}$—, $R_4$—$(O)_{b2}$— and $R_5$—$(O_1)_{b3}$— together are a radical of the formula

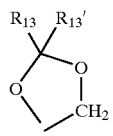

wherein $R_{13}$ and $R_{13}'$ are each independently of the other H, $C_1$–$C_8$-alkyl, $C_3$–$C_8$-cycloalkyl, benzyl or phenyl;

Z is bivalent —O—, —NH— or —$NR_{12}$—, wherein $R_{12}$ is linear or branched $C_1$–$C_6$-alkyl;

$Z_1$ is —O—, —O—(O)C—, —C(O)—O— or —O—C(O)—O—;

a, b1, b2 and b3 are each independently of the other 0 or 1;

$R_6$ independently has the same definitions as $R_1$ or is linear $C_3$–$C_{18}$-alkylene;

$Z_2$ is a direct bond or —O—$(CH_2)_d$— wherein d is an integer from 1 to 6 and the terminal $CH_2$ group of which is linked to the adjacent T in formula (10c);

T is bivalent —O—, —NH—, —S—, $C_1$–$C_8$-alkylene or

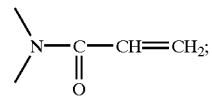

$R_8$ is linear or branched $C_1$–$C_8$-alkyl, $C_2$–$C_8$-alkenyl or $C_6$–$C_{10}$-aryl-$C_1$–$C_8$-alkyl;

$R_9$ independently of $R_8$ has the same definitions as $R_8$ or is $C_6$–$C_{10}$-aryl, or $R_8$ and $R_9$ together are —$(CH_2)_e$— wherein e is an integer from 2 to 6;

$R_{10}$ and $R_{11}$ are each independently of the other linear or branched $C_1$–$C_8$-alkyl that may be substituted by $C_1$–$C_4$-alkoxy, or $C_6$–$C_{10}$-aryl-$C_1$–$C_8$-alkyl or $C_2$–$C_8$-alkenyl; or $R_{10}$ and $R_{11}$ together are —$(CH_2)_{f1}$—$Z_3$—$(CH_2)_{f2}$— wherein $Z_3$ is a direct bond, —O—, —S— or —$NR_7$—, and $R_7$ is H or $C_1$–$C_8$-alkyl and f1 and f2 are each independently of the other an integer from 2 to 4;

$R_{29}$ is a radical of formula

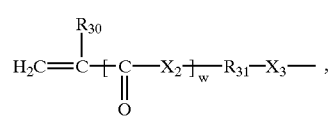

wherein $R_{30}$ is hydrogen or methyl, $R_{31}$ is $C_1$–$C_{12}$-alkylene, $C_1$–$C_6$-alkylenephenylene or phenylene-$C_1$–$C_6$-alkylene, or if w is 0 may also be a direct bond, w is 0 or 1, and $X_2$ and $X_3$ are each independently of the other —O— or —NH—;

subject to the provisos that b1 and b2 are each 0 when $R_5$ is H; that the total of (b1+b2+b3) is not exceeding 2; and that a is 0 when $R_2$ is a direct bond.

11. A process according to claim 1, wherein in step (b) a hydrophilic monomer is graft polymerized onto the polymerization initiator-modified polymer brushes, and wherein the hydrophilic monomer is selected from the group consisting of hydroxy-substituted $C_1$–$C_4$-alkyl acrylates and methacrylates, acrylamide, methacrylamide, mono- and di-$C_1$–$C_4$ alkylacrylamides and -methacrylamides, ethoxylated acrylates and methacrylates, hydroxy-substituted $C_1$–$C_4$-alkylacrylamides and methacrylamides, hydroxy-substituted $C_1$–$C_4$-alkyl vinyl ethers, sodium ethylenesulfonate, sodium styrenesulfonate, 2-acrylamido-2-methylpropanesulfonic acid, N-vinylpyrrole, N-vinylsuccinimide, N-vinylpyrrolidone, 2- and 4-vinylpyridine, vinylically unsaturated carboxylic acids having a total of from 3 to 5 carbon atoms, amino-, mono-$C_1$–$C_4$-alkylamino- or di-$C_1$–$C_4$-alkylamino-$C_1$–$C_4$-alkyl acrylates and methacrylates, vinylacetate and allyl alcohol.

12. A process according to claim 1, wherein in step (b) a macromonomer of formula

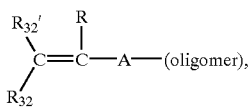  (4)

is graft polymerized onto the polymerization initiator-modified polymer brushes, wherein $R_{32}$ is hydrogen, $C_1$–$C_6$-alkyl or a radical —COOR';
R, R' and $R_{32}'$ are each independently of the other hydrogen or $C_1$–$C_6$-alkyl;
A is a direct bond or is a radical of formula —C(O)—$(A_1)_n$—X—  (5a) or —$(A_2)_m$—NH—C(O)—X—  (5b); or —$(A_2)_m$—X—C(O)—  (5c); or —C(O)—NH—C(O)—X—  (5d); or —C(O)—X—(alk*)—X—C(O)—  (5e); or A and $R_{32}$, together with the adjacent double bond, are a radical of formula

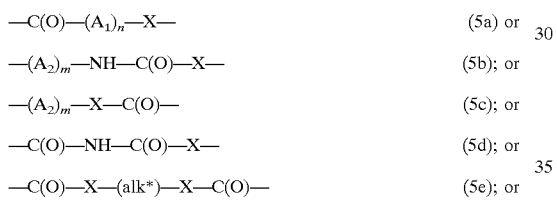  (5f)

$A_1$ is —O—$C_2$–$C_{12}$-alkylene which is unsubstituted or substituted by hydroxy, or is —O—$C_2$–$C_{12}$-alkylene-NH—C(O)— or —O—$C_2$–$C_{12}$-alkylene-O—C(O)—NH—$R_{33}$—NH—C(O)— or —NH—(Alk*)—C(O), wherein (Alk*) is $C_1$–$C_6$-alkylene and $R_{33}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_1$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;
$A_2$ is $C_1$–$C_8$-alkylene; phenylene or benzylene;
m and n are each independently of the other the number 0 or 1;
X, $X_1$ and X' are each independently of the other a bivalent group —O— or —NR", wherein R" is hydrogen or $C_1$–$C_6$-alkyl;

(alk*) is $C_2$–$C_{12}$-alkylene; and (oligomer) denotes
(i) the radical of a telomer of formula

  (6a), wherein (alk) is $C_2$–$C_{12}$-alkylene,
Q is a monovalent group that is suitable to act as a polymerization chain-reaction terminator,
p and q are each independently of another an integer from 0 to 350, wherein the total of (p+q) is an integer from 2 to 350,
and B and B' are each independently of the other a 1,2-ethylene radical derivable from a copolymerizable vinyl monomer by replacing the vinylic double bond by a single bond, at least one of the radicals B and B' being substituted by a hydrophilic substituent; or
(i) the radical of an oligomer of the formula

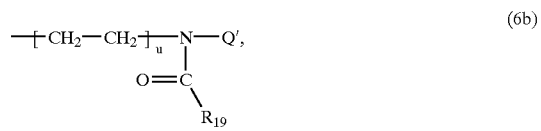  (6b)

wherein $R_{19}$ is hydrogen or unsubstituted or hydroxy-substituted $C_1$–$C_{12}$-alkyl, u is an integer from 2 to 250 and Q' is a radical of a polymerization initiator; or
(iii) the radical of formula

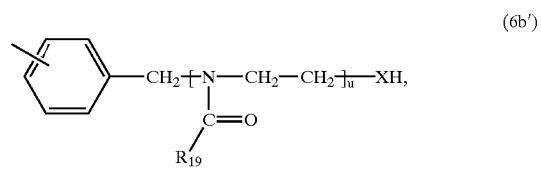  (6b')

wherein $R_{19}$, X and u are as defined above, or
(iv) the radical of an oligomer of formula

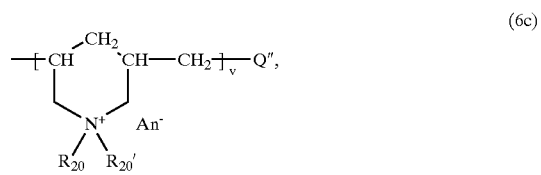  (6c)

wherein $R_{20}$ and $R_{20}'$ are each independently $C_1$–$C_4$-alkyl, An⁻ is an anion, v is an integer from 2 to 250, and Q" is a monovalent group that is suitable to act as a polymerization chain-reaction terminator; or
(v) the radical of an oligopeptide of formula

 (6d) or

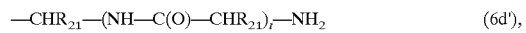 (6d'), wherein $R_{21}$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—$NH_2$ and t is an integer from 2 to 250, or the radical of an oligopeptide based on proline or hydroxyproline; or
(vi) the radical of a polyalkylene oxide of formula —(alk** -O)$_z$—[CH$_2$—CH$_2$—O]$_r$—[CH$_2$—CH(CH$_3$)—O]$_s$—R$_{34}$), wherein R$_{34}$ is hydrogen or C$_1$–C$_{24}$-alkyl, (alk ) is C$_2$–C$_4$-alkylene, z is 0 or 1, r and s are each independently an integer from 0 to 250 and the total of (r+s) is from 2 to 250; or (vii) the radical of an oligosaccharide, subject to the provisos that A is not a direct bond if (oligomer) is a radical of formula (6a);

A is a radical of formula (5a), (5b) or (5d) or A and R$_{32}$, together with the adjacent double bond, are a radical of formula (5f) if (oligomer) is a radical of formula (6b), (6c), (6d) or (6e) or is the radical of an oligosaccharide;

A is a direct bond if (oligomer) is a radical of formula (6b'); and

A is a radical of formula (5c) or (5e) if (oligomer) is a radical of formula (6d').

13. A process according to claim 12, wherein the macromonomer is of formula (4a)

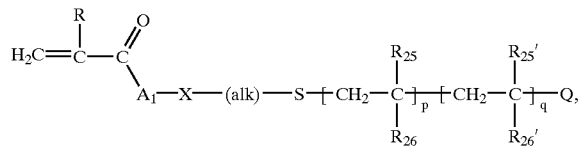

wherein R is hydrogen or methyl, A$_1$ is —O—(CH$_2$)$_{2-4}$—, —O—CH$_2$—CH(OH)—CH$_2$— or a radical —O—(CH$_2$)$_{2-4}$—NH—C(O)—, X is —O— or —NH—, (alk) is C$_2$–C$_4$-alkylene, Q is a monovalent group that is suitable to act as a polymerization chain-reaction terminator, p is an integer from 5 to 50, R$_{25}$ and R$_{25}$' are each independently of the other hydrogen or methyl, and R$_{26}$ and R$_{26}$' are each independently a radical —COOY, wherein Y is C$_1$–C$_2$-alkyl, C$_2$–C$_3$-alkyl, which is substituted by hydroxy, amino or N,N-di-C$_1$–C$_2$-alkylamino, or is a radical —C$_2$–C$_4$-alkylene-NH—C(O)—O—G wherein —O—G is the radical of trehalose or a cyclodextrin fragment with a maximum of 8 sugar units; or a radical —CO—NY$_1$Y$_2$, wherein Y$_1$ and Y$_2$ are each independently of the other hydrogen or C$_1$–C$_4$-alkyl which is unsubstituted or substituted by hydroxy, or Y$_1$ and Y$_2$ together with the adjacent N-atom form a N-C$_1$–C$_2$-alkyl-piperazino or morpholino ring; or a heterocyclic radical selected from the group consisting of N-pyrrolidonyl, 2- or 4-pyridinyl, 2-methylpyridin-5-yl, 2-, 3- oder 4-hydroxypyridinyl, N-ε-caprolactamyl, N-imidazolyl, 2-methylimidazol-1-yl, N-morpholinyl and 4-N-methylpiperazin-1-yl.

14. A process according to claim 12, wherein the macromonomer is of formula (4b)

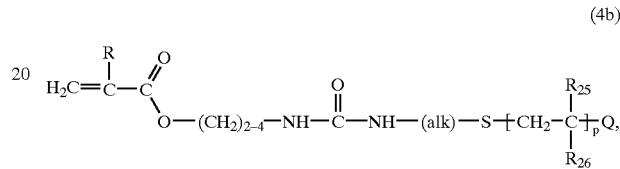

wherein R is hydrogen or methyl, (alk) is C$_2$–C$_4$-alkylene, R$_{25}$ is hydrogen or methyl, p is an integer of 5 to 50, Q is as defined in claim 12, and R$_{26}$ is a radical —CONH$_2$, —CON(CH$_3$)$_2$ or

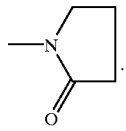

* * * * *